(12) United States Patent
Clark

(10) Patent No.: US 7,805,254 B2
(45) Date of Patent: Sep. 28, 2010

(54) SYSTEM, METHOD AND COMPUTER PROGRAM FOR NON-BINARY SEQUENCE COMPARISON

(75) Inventor: Jeffrey M. Clark, Lancaster, TX (US)

(73) Assignee: Bioinformatica, LLC, Texarkana, AR (US)

( * ) Notice: Subject to any disclaimer, the term of this patent is extended or adjusted under 35 U.S.C. 154(b) by 622 days.

(21) Appl. No.: 11/774,904

(22) Filed: Jul. 9, 2007

(65) Prior Publication Data

US 2008/0040048 A1 Feb. 14, 2008

Related U.S. Application Data

(63) Continuation of application No. 11/378,284, filed on Mar. 20, 2006, now Pat. No. 7,263,444.

(60) Provisional application No. 60/662,943, filed on Mar. 18, 2005.

(51) Int. Cl.
*G06F 19/00* (2006.01)
(52) U.S. Cl. .......................... 702/20; 702/19
(58) Field of Classification Search ................. None
See application file for complete search history.

(56) References Cited

U.S. PATENT DOCUMENTS

2004/0018535 A1 1/2004 Sampath et al.

FOREIGN PATENT DOCUMENTS

WO 2005024562 A2 3/2005

OTHER PUBLICATIONS

Rice et al. (TIG, vol. 16, No. 6, p. 276-277, Jun. 2000).*
Wheeler (Weight Matrices for Sequence Similarity Scoring; Electronic Resource: [www.techfak.uni-bielefeld.de/bcd/Curric/PrwAli/nodeD.html]; Accessed on Feb. 25, 2010).*
Hastad et al. (Mol. Biol. Evol. 15(11):1381-1389. 1998).*
Carver et al. (Bioinformatics, vol. 19, No. 14, p. 1837-1843, 2003).*
Partial European Search Report, Application No. EP 08164915, dated Jan. 27, 2009.
Accelrys, Inc.—GCG Manual Version, Version 10.3, 2002.
Almeida, J.S., et al., "Analysis of genomic sequences by Chaos Game Representation," Bioinformatics, vol. 17, No. 5, p. 429-437, Oxford University Press, 2001.
Altschul, et al., "Basic Local Alignment Search Tool," J. Mol. Biol., vol. 215, P. 403-410, 1990.
Baxevanis, A.D. et al., "Bioinformatics: A Practical Guide to the Analysis of Genes and Proteins" Chapter 10—"Predictive Methods Using DNA Sequences" pp. 233-252, Wiley-Liss, Inc., 2001.
Pedersen, J.S, et al., "Gene finding with a hidden Markov model of genome structure and evolution," Bioinformatics, vol. 19, No. 2, p. 219-227, 2003.
Vigna, S., et al., "Alignment-free sequence comparison—a review," Bioinformatics, vol. 19, No. 4, p. 513-523, 2003.
Supplementary Partial European Search Report, Application No. EP 06 73 8815, dated Jun. 12, 2008.
International Search Report, International Application No. PCT/US06/09808, with Written Opinion of the International Searching Authority, mailed Jan. 5, 2007.
Poland, D., "Long-range correlations in the helix free energy distribution in DNA," Biophysical Chemistry, vol. 106, No. 3, 2003, pp. 275-303.
Shu, J-J, et al., "Pairwise alignment of the DNA sequence using hypercomplex number representation," Bulletin of Mathematical Biology, vol. 66, No. 5, pp. 1423-1438 (2004).

\* cited by examiner

*Primary Examiner*—Karlheinz R Skowronek
(74) *Attorney, Agent, or Firm*—Ping Wang; Morris, Manning & Martin, LLP

(57) ABSTRACT

A system and method for performing non-binary comparison of biological sequences includes a new measure $\omega_0$, which is a non-binary counting measure that is used in a stand alone module called VaSSA-1. This measure obtains substantially more information about sequences and comparisons between them than is gathered by conventional bioinformatics techniques.

9 Claims, 40 Drawing Sheets

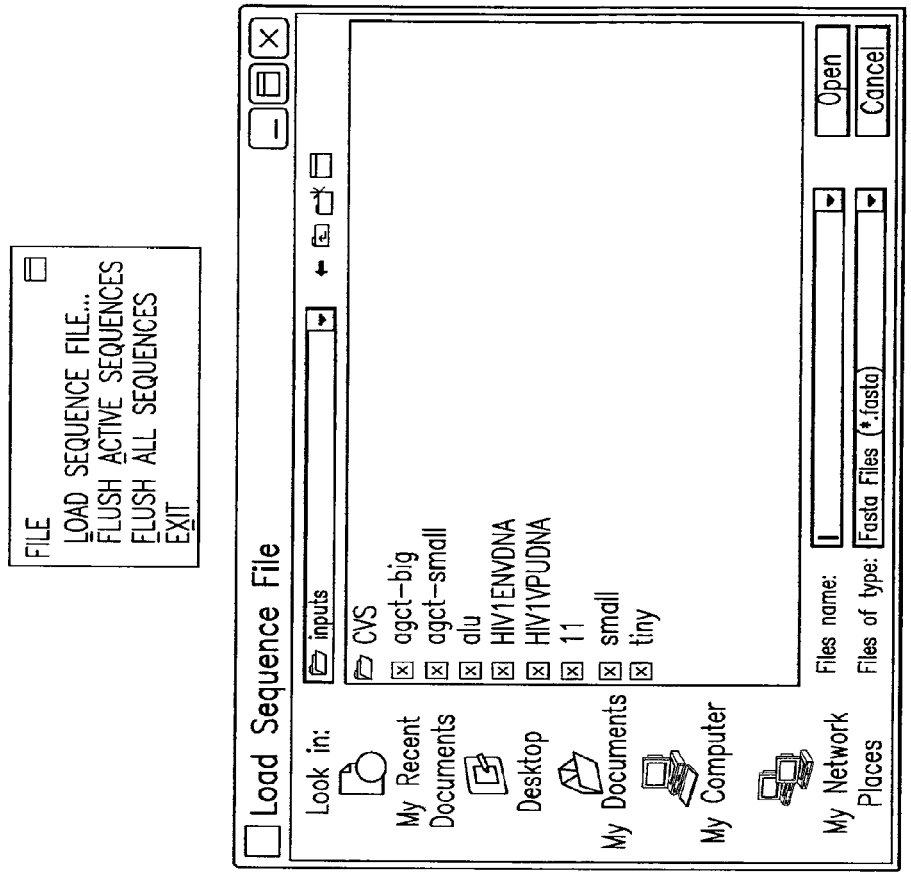

- LOAD SEQUENCES
  - MULTIPLE FASTA FORMATTED SEQUENCE FILES CAN BE LOADED
  - EACH SEQUENCE IS ASSIGN A UNIQUE REFERENCE NUMBER
  - EACH SEQUENCE IS CHECKED FOR VALID CHARACTERS
- FLUSH ACTIVE SEQUENCES
  - ANY INDIVIDUAL SEQUENCE FILE CAN BE FLUSHED FROM MEMORY. THE ORIGINAL REFERENCE NUMBERS ARE PRESERVED
- FLUSH LOADED SEQUENCES
  - ALL LOADED SEQUENCES CAN BE FLUSHED OUT OF MEMORY
  - USER CAN START OVER

FIG.4

SEQUENCE NOTEBOOK VIEWER

| □ VSSA CQuence, Inc. | | | | | | | | | | | | | ☐ ☒ |
|---|---|---|---|---|---|---|---|---|---|---|---|---|---|
| File  Edit  Reports  Analysis  Plots  Options  Help | | | | | | | | | | | | | |
| HIV1ENVDNA.fasta (629) | alu.fasta (327) | J1.fasta (71) | small.fasta (2) | | | | | | | | | | |
| Ref# | Sequence | | | | | | | | | | | | Length |
| 630 | >gnl\|alu\|HSU14568 ***ALU WARNING: Human Alu-Sb subfamily consensu... | | | | | | | | | | | | 288 |
| 631 | >gnl\|alu\|HSU14574 ***ALU WARNING: Human Alu-Sx subfamily consensu... | | | | | | | | | | | | 290 |
| 632 | >gnl\|alu\|HSU14573 ***ALU WARNING: Human Alu-Sq subfamily consensu... | | | | | | | | | | | | 291 |
| 633 | >gnl\|alu\|HSU14572 ***ALU WARNING: Human Alu-Sp subfamily consensu... | | | | | | | | | | | | 291 |
| 634 | >gnl\|alu\|HSU14571 ***ALU WARNING: Human Alu-Sc subfamily consensu... | | | | | | | | | | | | 287 |
| 635 | >gnl\|alu\|HSU14570 ***ALU WARNING: Human Alu-Sb2 subfamily consens... | | | | | | | | | | | | 296 |
| 636 | >gnl\|alu\|HSU14567 ***ALU WARNING: Human Alu-J subfamily consensus... | | | | | | | | | | | | 290 |
| 637 | >gnl\|alu\|HSU14569 ***ALU WARNING: Human Alu-Sb1 subfamily consens... | | | | | | | | | | | | 288 |
| 638 | >gnl\|alu\|M38064_HSAL002939 (Alu-Sx) | | | | | | | | | | | | 379 |
| 639 | >gnl\|alu\|M25718_HSAL002875 (Alu-Sp) | | | | | | | | | | | | 339 |
| 640 | >gnl\|alu\|M11228_HSAL002744 (Alu-Sp) | | | | | | | | | | | | 337 |
| 641 | >gnl\|alu\|M38180_HSAL001409 (Alu-J) | | | | | | | | | | | | 339 |
| 642 | >gnl\|alu\|L05920_HSAL001628 (Alu-J) | | | | | | | | | | | | 327 |

- UPON LOADING EACH SEQUENCE FILE A SUMMARY REPORT NOTEBOOK PAGE IS GENERATED
- THE SEQUENCE FILE NAME AND NUMBER OF SEQUENCES IS DISPLAYED ON EACH PAGE TAB
- EACH SEQUENCE FILE SUMMARY CAN BE VIEWED BY CLICKING ON IT'S RESPECTIVE PAGE TAB
- ANY INDIVIDUAL SEQUENCE FILE OR ALL SEQUENCE FILES CAN BE FLUSHED. THE ORIGINAL REFERENCE NUMBERS ARE PRESERVED
- AS SEQUENCE FILES ARE DELETED THE NOTEBOOK PAGE IS DELETED

FIG.5

REPORTS > SEQUENCE SUMMARY

- DISPLAYS A SUMMARY OF ALL LOADED SEQUENCES

- INCLUDED ARE THE UNIQUE REFERENCE NUMBER, THE SEQUENCE HEADER, AND THE SEQUENCE LENGTH

| Sequence Summary (327 total) | | |
|---|---|---|
| Ref# | Sequence | Length |
| 1 | >gnl\|alu\|HSU14568 ***ALU WARNING: Human... | 288 |
| 2 | >gnl\|alu\|HSU14574 ***ALU WARNING: Human... | 290 |
| 3 | >gnl\|alu\|HSU14573 ***ALU WARNING: Human... | 291 |
| 4 | >gnl\|alu\|HSU14572 ***ALU WARNING: Human... | 291 |
| 5 | >gnl\|alu\|HSU14571 ***ALU WARNING: Human... | 287 |
| 6 | >gnl\|alu\|HSU14570 ***ALU WARNING: Human... | 296 |
| 7 | >gnl\|alu\|HSU14567 ***ALU WARNING: Human... | 290 |
| 8 | >gnl\|alu\|HSU14569 ***ALU WARNING: Human... | 288 |
| 9 | >gnl\|alu\|M38064_HSAL002939 (Alu-Sx) | 379 |
| 10 | >gnl\|alu\|M25718_HSAL002875 (Alu-Sp) | 339 |
| 11 | >gnl\|alu\|M11228_HSAL002744 (Alu-Sp) | 337 |
| 12 | >gnl\|alu\|M38180_HSAL001409 (Alu-J) | 339 |
| 13 | >gnl\|alu\|L05920_HSAL001628 (Alu-J) | 327 |
| 14 | >gnl\|alu\|L10820_HSAL001794 (Alu-J) | 344 |
| 15 | >gnl\|alu\|X02228_HSAL000635 (Alu-Sx) | 353 |
| 16 | >gnl\|alu\|M38180_HSAL001408 (Alu-Sx) | 326 |
| 17 | >gnl\|alu\|L05173_HSAL001270 (Alu-Sq) | 336 |
| 18 | >gnl\|alu\|M29484_HSAL002265 (Alu-J) | 353 |
| 19 | >gnl\|alu\|M90058_HSAL002952 (Alu-J) | 341 |

FIG.6

REPORTS > VIEW SEQUENCES

- DISPLAYS THE CONTENTS OF EACH LOADED SEQUENCE

- INCLUDED ARE THE UNIQUE REFERENCE NUMBER AND THE SEQUENCE CONTENTS IN FASTA FORMAT

| Ref# | Sequence |
|---|---|
| 1 | >gnl\|alu\|HSU14568 ***ALU WARNING: Human Alu-Sb subfamil...<br>GGCCGGGCGCGGTGGCTCACGCCTGTAATCCCAGCACTTTGGGAGGCCGAGGCGGGCGGA<br>TCACGAGGTCAGGAGATCGAGACCATCCTGGCTAACACGGTGAAACCCCGTCTCTACTAA<br>AAATACAAAAATTAGCCGGGCGTGGTGGCGGGCGCCTGTAGTCCCAGCTACTCGGGAGGC<br>TGAGGCAGGAGAATGGCGTGAACCCGGGAGGCGGAGCTTGCAGTGAGCCGAGATCGCGCC<br>ACTGCACTCCAGCCTGGGCGACAGAGCGAGACTCCGTCTCAAAAAAAA |
| 2 | >gnl\|alu\|HSU14574 ***ALU WARNING: Human Alu-Sx subfamil...<br>GGCCGGGCGCGGTGGCTCACGCCTGTAATCCCAGCACTTTGGGAGGCCGAGGCGGGCGGA<br>TCACCTGAGGTCAGGAGTTCGAGACCAGCCTGGCCAACATGGTGAAACCCCGTCTCTACT<br>AAAAATACAAAAATTAGCCGGGCGTGGTGGCGCGCGCCTGTAATCCCAGCTACTCGGGAG<br>GCTGAGGCAGGAGAATCGCTTGAACCCGGGAGGCGGAGGTTGCAGTGAGCCGAGATCGCG<br>CCACTGCACTCCAGCCTGGGCGACAGAGCGAGACTCCGTCTCAAAAAAAA |
| 3 | >gnl\|alu\|HSU14573 ***ALU WARNING: Human Alu-Sq subfamil...<br>GGCCGGGCGCGGTGGCTCACGCCTGTAATCCCAGCACTTTGGGAGGCCGAGGCGGGTGGA<br>TCACCTGAGGTCAGGAGTTCGAGACCAGCCTGGCCAACATGGTGAAACCCCGTCTCTACT<br>AAAAATACAAAAATTAGCCGGGCGTGGTGGCGCGCGCCTGTAATCCCAGCTACTCGGGAG<br>GCTGAGGCAGGAGAATCGCTTGAACCCGGGAGGCGGAGGTTGCAGTGAGCCGAGATCGCG<br>CCACTGCACTCCAGCCTGGGCAACAAGAGCGAAACTCCGTCTCAAAAAAAA |
| 4 | >gnl\|alu\|HSU14572 ***ALU WARNING: Human Alu-Sp subfamil...<br>GGCCGGGCGCGGTGGCTCACGCCTGTAATCCCAGCACTTTGGGAGGCCGAGGCGGGCGGA<br>TCACCTGAGGTCGGGAGTTCGAGACCAGCCTGACCAACATGGAGAAACCCCGTCTCTACT<br>AAAAATACAAAAATTAGCCGGGCGTGGTGGCGCATGCCTGTAATCCCAGCTACTCGGGAG<br>GCTGAGGCAGGAGAATCGCTTGAACCCGGGAGGCGGAGGTTGCGGTGAGCCGAGATCGCG<br>CCATTGCACTCCAGCCTGGGCAACAAGAGCGAAACTCCGTCTCAAAAAAAA |

FIG. 7

REPORTS > VIEW SEQUENCES STATS

- DISPLAYS STATISTICAL INFORMATION ABOUT EACH LOADED SEQUENCE
- INCLUDED ARE THE UNIQUE REFERENCE NUMBER, THE SEQUENCE HEADER, AND A COUNT OF EACH STANDARD SEQUENCE CHARACTER
- AN ERROR IS GENERATED WHEN A SEQUENCE CHARACTER ISN'T RECOGNIZED

Sequence Statistics (327 total)

| Ref# | Sequence | Length | A | G | C | T | U | M | R | W | S | Y | K | V | H | D | B | N | . | Error |
|---|---|---|---|---|---|---|---|---|---|---|---|---|---|---|---|---|---|---|---|---|
| 1 | >gnl\|alu\|HSU14568 ***ALU WARNING: Human... | 288 | 68 | 98 | 80 | 42 | 0 | 0 | 0 | 0 | 0 | 0 | 0 | 0 | 0 | 0 | 0 | 0 | 0 | 0 |
| 2 | >gnl\|alu\|HSU14574 ***ALU WARNING: Human... | 290 | 68 | 96 | 82 | 44 | 0 | 0 | 0 | 0 | 0 | 0 | 0 | 0 | 0 | 0 | 0 | 0 | 0 | 0 |
| 3 | >gnl\|alu\|HSU14573 ***ALU WARNING: Human... | 291 | 71 | 95 | 80 | 45 | 0 | 0 | 0 | 0 | 0 | 0 | 0 | 0 | 0 | 0 | 0 | 0 | 0 | 0 |
| 4 | >gnl\|alu\|HSU14572 ***ALU WARNING: Human... | 291 | 72 | 94 | 80 | 45 | 0 | 0 | 0 | 0 | 0 | 0 | 0 | 0 | 0 | 0 | 0 | 0 | 0 | 0 |
| 5 | >gnl\|alu\|HSU14571 ***ALU WARNING: Human... | 287 | 69 | 94 | 80 | 44 | 0 | 0 | 0 | 0 | 0 | 0 | 0 | 0 | 0 | 0 | 0 | 0 | 0 | 0 |
| 6 | >gnl\|alu\|HSU14570 ***ALU WARNING: Human... | 296 | 71 | 102 | 78 | 45 | 0 | 0 | 0 | 0 | 0 | 0 | 0 | 0 | 0 | 0 | 0 | 0 | 0 | 0 |
| 7 | >gnl\|alu\|HSU14567 ***ALU WARNING: Human... | 290 | 67 | 97 | 82 | 44 | 0 | 0 | 0 | 0 | 0 | 0 | 0 | 0 | 0 | 0 | 0 | 0 | 0 | 0 |
| 8 | >gnl\|alu\|HSU14569 ***ALU WARNING: Human... | 288 | 70 | 96 | 80 | 42 | 0 | 0 | 0 | 0 | 0 | 0 | 0 | 0 | 0 | 0 | 0 | 0 | 0 | 0 |
| 9 | >gnl\|alu\|M38064_HSAL002939 (Alu-Sx) | 379 | 120 | 100 | 88 | 71 | 0 | 0 | 0 | 0 | 0 | 0 | 0 | 0 | 0 | 0 | 0 | 0 | 0 | 0 |
| 10 | >gnl\|alu\|M25718_HSAL002875 (Alu-Sp) | 339 | 104 | 110 | 85 | 40 | 0 | 0 | 0 | 0 | 0 | 0 | 0 | 0 | 0 | 0 | 0 | 0 | 0 | 0 |
| 11 | >gnl\|alu\|M11228_HSAL002744 (Alu-Sp) | 337 | 107 | 93 | 80 | 57 | 0 | 0 | 0 | 0 | 0 | 0 | 0 | 0 | 0 | 0 | 0 | 0 | 0 | 0 |
| 12 | >gnl\|alu\|M38180_HSAL001409 (Alu-J) | 339 | 110 | 90 | 72 | 67 | 0 | 0 | 0 | 0 | 0 | 0 | 0 | 0 | 0 | 0 | 0 | 0 | 0 | 0 |
| 13 | >gnl\|alu\|L05920_HSAL001628 (Alu-J) | 327 | 117 | 93 | 53 | 64 | 0 | 0 | 0 | 0 | 0 | 0 | 0 | 0 | 0 | 0 | 0 | 0 | 0 | 0 |

FIG. 8

ANALYSIS > ALIGN SEQUENCES

- A BASE AND TARGET SEQUENCE CAN BE CHOSEN FROM THE LIST OF LOADED SEQUENCES

- THE ALIGNMENT STATISTICS CAN OPTIONALLY BE DISPLAYED IN THE ALIGNMENT REPORT

- THE OMEGA SIMILARITY SCORE CAN OPTIONALLY BE DISPLAYED IN THE ALIGNMENT REPORT

ALIGNED SEQUENCES REPORT

ANALYSIS > QUERY REPEATS

- A BASE SEQUENCE IS CHOSEN FROM THE LIST OF LOADED SEQUENCES
- A TARGET SEQUENCE IS CHOSEN WHICH WILL BE SEARCHED FOR IN THE BASE
- A THRESHOLD IS SPECIFIED WHICH RELAXES THE SEARCH
- THE BASE OR TARGET SEQUENCE CAN BE REVERSED
- THE OMEGA FORMULA CAN BE ADJUSTED

QUERY REPEATS REPORT

QUERY OF BASE: 1 target=agct, subtargets=agc gct length=360, query_hits=1, sub_query_hits=12

Base: 1    TTCTTTCATGGGGAAGCAGATTTGGGTACCACCCCAAGTATTGACTCACCCATCAACAACC 60
                                 ***

Base: 61   GCTATGTATTTCGTACATTACTGCCAGCCACCATGAATATTGTACAGTACCATAAATACT 120
                   ***                              ~1202

Base: 121  TGACCACCTGTAGTACATAAAAACCCAATCCACATCAAAAACCCTCCCCTCATGCTTACAA 180
                                                              ***    *

Base: 181  GCAAGTACACAGCAATCAACCTTCAACTATCACACATCAACTGCAAGCCACCTCT 240
              *                                        ***

Base: 241  CCCCCACTAGGATACCAACAAAGCTACCCATCCTTAACAGTACATAGCACATAAAGCCAT 300
                                        ^^^~1201       *    *

Base: 301  TTACCGTACATAGCACATTACAGTCAAATCCCTTCCTGTCCCCATGGATGACCCCCCTCA 360
                   ***

FIG.12

ANALYSIS > OMEGA SUB ZERO

- ONE BASE OR ALL SEQUENCES CAN BE CHOSEN FROM THE LIST OF LOADED SEQUENCES

- THE REPORT CAN BE SORTED BY REFERENCE NUMBER, LENGTH, OR OMEGA SCORE

- THE BASE SEQUENCE CAN BE REVERSED

- THE OMEGA FORMULA CAN BE ADJUSTED

OMEGA SUB ZERO REPORT

☐ Omega Sub Zero sorted by ref

| Ref# | Sequence | Length | Omega |
|---|---|---|---|
| 1 | >gnl\|alu\|HSU14568 ***ALU WARNING: Human... | 288 | 2115 |
| 2 | >gnl\|alu\|HSU14574 ***ALU WARNING: Human... | 290 | 2114 |
| 3 | >gnl\|alu\|HSU14573 ***ALU WARNING: Human... | 291 | 2045 |
| 4 | >gnl\|alu\|HSU14572 ***ALU WARNING: Human... | 291 | 2055 |
| 5 | >gnl\|alu\|HSU14571 ***ALU WARNING: Human... | 287 | 2128 |
| 6 | >gnl\|alu\|HSU14570 ***ALU WARNING: Human... | 296 | 2161 |
| 7 | >gnl\|alu\|HSU14567 ***ALU WARNING: Human... | 290 | 2144 |
| 8 | >gnl\|alu\|HSU14569 ***ALU WARNING: Human... | 288 | 2063 |
| 9 | >gnl\|alu\|M38064_HSAL002939 (Alu-Sx) | 379 | 2665 |
| 10 | >gnl\|alu\|M25718_HSAL002875 (Alu-Sp) | 339 | 2487 |
| 11 | >gnl\|alu\|M11228_HSAL002744 (Alu-Sp) | 337 | 2278 |
| 12 | >gnl\|alu\|M38180_HSAL001409 (Alu-J) | 339 | 2130 |
| 13 | >gnl\|alu\|L05920_HSAL001628 (Alu-J) | 327 | 2096 |
| 14 | >gnl\|alu\|L10820_HSAL001794 (Alu-J) | 344 | 2369 |

FIG.14

ANALYSIS > QUERY OMEGA REPEATS

- A BASE SEQUENCE IS CHOSEN FROM THE LIST OF LOADED SEQUENCES
- A TARGET SEQUENCE IS CHOSEN WHICH WILL BE SEARCHED FOR IN THE BASE
- A THRESHOLD IS SPECIFIED WHICH RELAXES THE SEARCH
- THE BASE OR TARGET SEQUENCE CAN BE REVERSED
- THE OMEGA FORMULA CAN BE ADJUSTED

QUERY OMEGA REPEATS REPORT

☐ QUERY OF BASE: 1 target=agct, subtargets=agc gct length=360, query_hits=2, sub_query_hits=15 - (used OmegaSubN)

Base: 1    TTCTTTCATGGGAAGCAGATTTGGGTACCCCAAGTATTGACTCACCCATCAACAACC 60
                                    ***

Base: 61   GCTATGTATTTCGTACATTACTGCCAGCACCATGAATATTGTACAGTACCATAAATACT 120
             *  *

Base: 121  TGACCACCTGTAGTACATAAAAACCCAATCCACATCAAAACCCTCCCCTCATGCTTACAA 180
                  *

Base: 181  GCAAGTACAGCAATCAACCTTCAACTATCACACATCAACTGCAACTCCAAAGCCACCTCT 240
                 *                                      *    *

Base: 241  CCCCCACTAGGATACCAACAACAAAGCTACCCATCCTTAACAGTACATAGCACATAAAGCCAT 300
                                ^^^                              *   *

Base: 301  TTACCGTACATAGCACACATTACAGTCAAATCCCTTCCTGTCCCCATGGATGACCCCCTCA 360
              ***

FIG.16

ANALYSIS > CALCULATE SLOPES

- A BASE SEQUENCE IS CHOSEN FROM THE LIST OF LOADED SEQUENCES

- THE BASE SEQUENCE CAN BE REVERSED

- THE OMEGA FORMULA CAN BE ADJUSTED

ANALYSIS > COMPARE SEQUENCES

- A BASE SEQUENCE IS CHOSEN FROM THE LIST OF LOADED SEQUENCES

- ALL OR ONE TARGET CAN BE CHOSEN FROM THE LIST OF LOADED SEQUENCES

- THE BASE OR TARGET SEQUENCE CAN BE REVERSED

- THE OMEGA FORMULA CAN BE ADJUSTED

COMPARE SEQUENCES REPORT

Comparison of Base: 3 and Targe...

| Ref# | Sequence | Length | Distance | Similar? |
|---|---|---|---|---|
| 31 | >750NY | 360 | 6.38467e-135 | yes |
| 47 | >899NY | 360 | 6.38467e-135 | yes |
| 15 | >L1011 | 360 | 6.8047e-130 | yes |
| 40 | >894NY | 360 | 6.8047e-130 | yes |
| 53 | >503 | 360 | 6.8047e-130 | yes |
| 68 | >513 | 360 | 6.8047e-130 | yes |
| 26 | >67 | 360 | 1.70918e-103 | no |
| 36 | >900NY | 360 | 4.13486e-093 | no |
| 49 | >499 | 360 | 4.13486e-093 | no |
| 61 | >497 | 360 | 2.34144e-067 | no |
| 62 | >498 | 360 | 2.34144e-067 | no |
| 65 | >510 | 360 | 2.34144e-067 | no |
| 39 | >895NY | 360 | 2.00304e-035 | no |
| 51 | >501 | 360 | 0.386719 | no |
| 52 | >502 | 360 | 0.386719 | no |

FIG.20

PLOTS > SPECTRAL ARRAY

- A BASE SEQUENCE IS CHOSEN FROM THE LIST OF LOADED SEQUENCES

- A TARGET IS CHOSEN FROM THE LIST OF LOADED SEQUENCES

- THE BASE OR TARGET SEQUENCE CAN BE REVERSED

SPECTRAL ARRAY PLOT FORMULAS $$f(z) = \sum_{l=0}^{\infty} C_l(z)$$

$$C_l(z) = \sum_{\lambda_1 + \lambda_2 + \cdots + \lambda_n = l} C_{\lambda_1 \lambda_2 \cdots \lambda_n} Z_1^{\lambda_1} Z_2^{\lambda_2} \cdots Z_n^{\lambda_n}, l = 0, 1, 2, \ldots$$

FIG.23

PLOTS > SINGLE STRAND

- A BASE SEQUENCE IS CHOSEN FROM THE LIST OF LOADED SEQUENCES
- A TARGET IS CHOSEN FROM THE LIST OF LOADED SEQUENCES
- THE BASE OR TARGET SEQUENCE CAN BE REVERSED
- THE OMEGA FORMULA CAN BE ADJUSTED

SINGLE STRAND PLOTS (CONT)
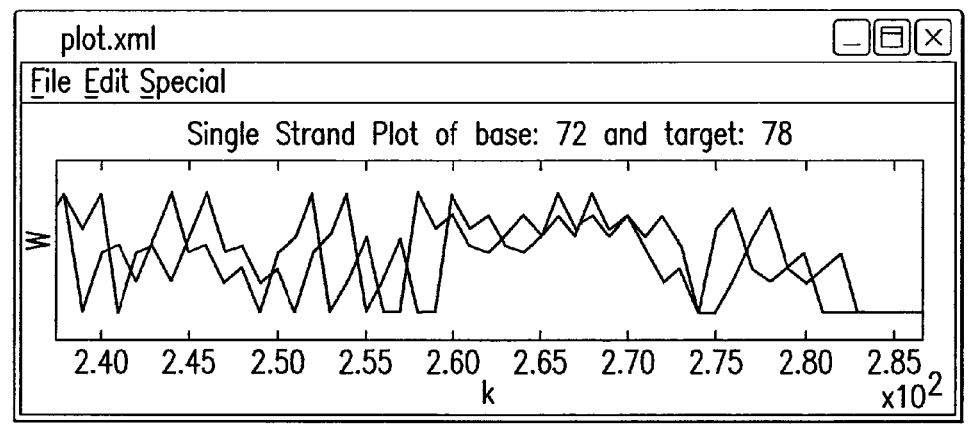
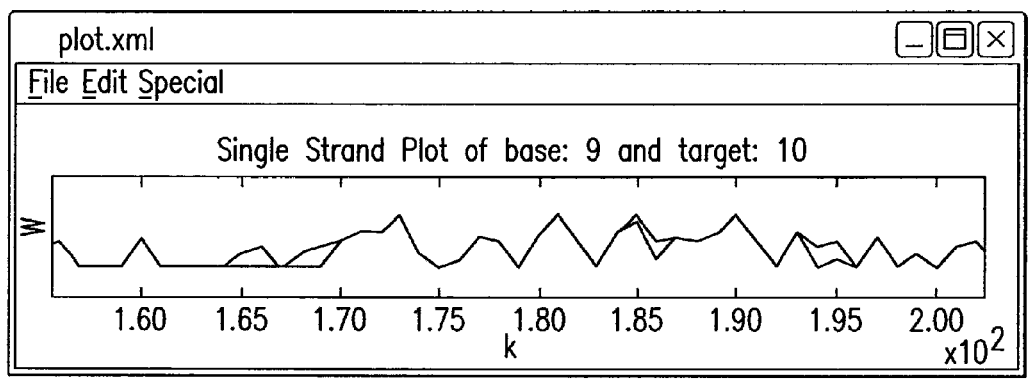
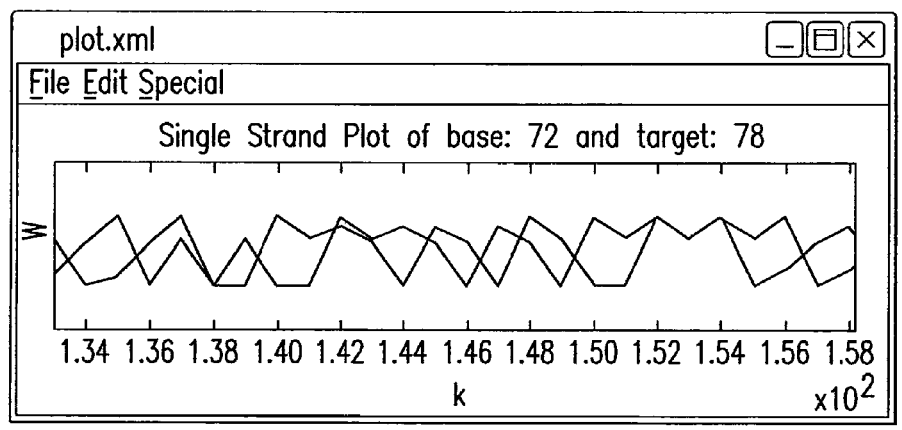
FIG.28

PLOTS > SLOPES

- A BASE SEQUENCE IS CHOSEN FROM THE LIST OF LOADED SEQUENCES

- THE BASE OR TARGET SEQUENCE CAN BE REVERSED

- THE OMEGA FORMULA CAN BE ADJUSTED

PLOTS > OMEGA SUB Ns

- A BASE SEQUENCE IS CHOSEN FROM THE LIST OF LOADED SEQUENCES

- THE BASE SEQUENCE CAN BE REVERSED

- THE OMEGA FORMULA CAN BE ADJUSTED

A/G
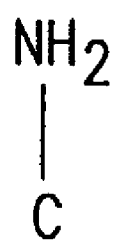 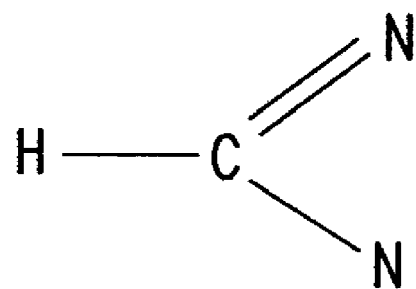
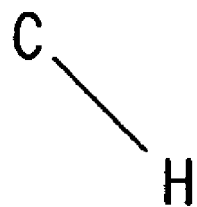
FIG.34A

G/A
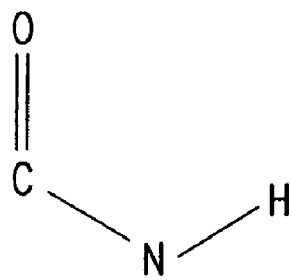
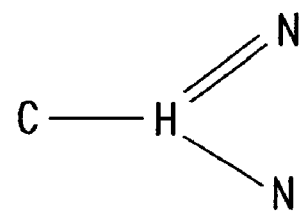
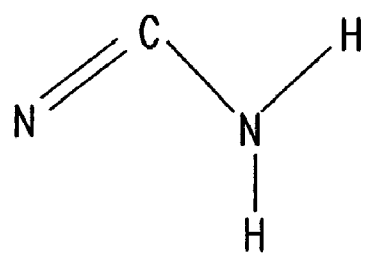
FIG.34C

SYSTEM, METHOD AND COMPUTER PROGRAM FOR NON-BINARY SEQUENCE COMPARISON This application is a continuation application of U.S. Ser. No. 11/378,284, filed Mar. 20, 2006, which claims priority from U.S. Provisional Application Ser. No. 60/662,943, filed Mar. 18, 2005. The entirety of all of the aforementioned applications is incorporated herein by reference.

FIELD

The present invention relates generally to bioinformatics, and more particularly to methods for determining the degree of similarity and difference between genetic sequences.

BACKGROUND

DNA sequences of entire genomes of different species are being determined at a rapid rate. It is incumbent on the bioinformatics community to understand these genomic structural variations and functions. Also, some finished versions of genome data contain gaps where data could not be acquired. These drafts of various genomic sequence data may consist of pieces of data whose relative order and orientation are difficult to determine. Dealing with such incomplete data places new demands upon integrative systems tools, particularly when two or more genomes are being compared. The bioinformatics community needs to be able to handle gaps more effectively.

In conventional approaches, handling comparisons across genomes is a major problem. For extremely similar sequences, there exist so called "greedy" alignment methods that compute optimal alignments. These algorithms allow gaps in the alignments and are extremely efficient, but work well only for very simple alignment scoring schemes. For richer scores (involved in large stretches of a single genome and comparing multiple genomes), these greedy methods lose their efficiency edge over dynamic programming.

Conventional alignment methods for three or more sequences are almost entirely geared toward comparison of protein sequences based on putative codons, sets of three nucleic acid bases encoding a single amino acid. This may be due to the fact that few examples exist of genomic sequence data from several similar species. Also, sequence comparisons and homology analyses are done on a binary basis. This conserves computational resources, but ignores biochemical information.

There is a need for an improved solution that overcomes shortcomings of conventional sequence alignment similarity and gene sequence comparison tools.

SUMMARY

A system for sequence analysis comprises an analysis module adapted to calculate a non-binary similarity score between a first nucleotide sequence and a second nucleotide sequence; a file management module; and a plot module.

In one embodiment, the system further comprises a report module, a user options module and/or a user help module.

In another embodiment, the file management module comprises a load sequences module, adapted to load at least one sequence file; a flush active sequence module, adapted to flush a sequence file from a memory; and a flush loaded sequence module, adapted to flush a loaded sequence file from the memory.

In another embodiment, the load sequence module comprises a loaded sequence display module, adapted to generate and display a summary report notebook page when a sequence is loaded, wherein the summary report notebook page is adapted to display a sequence file name and a number of sequences.

In another embodiment, the report module is adapted to generate and display a sequence summary, a listing of the contents of each loaded sequence, and/or statistical information about each loaded sequence.

In another embodiment, the analysis module comprises an align sequences module adapted to align a target sequence to a base sequence and to display an alignment report; an $\omega_0$ module adapted to calculate an $\omega_0$ score for a sequence and to display the $\omega_0$ score; a query repeat module adapted to locate multiple occurrences of the target sequence in the base sequence and to display the multiple occurrences; a query omega repeats module adapted to determine when repeated nucleotides are duplicates; a calculate slopes module adapted to calculate a slope for each nucleotide position in the base sequence and to display a slopes report; and a compare sequences module adapted to compare the target sequence to the base sequence and to display a similarity report.

In another embodiment, the plots module comprises a spectral array module, adapted to plot aligning coefficients for a base sequence and a target sequence; a single strand module adapted to plot a single strand for the base sequence and the target sequence; a slopes module adapted to calculate a slope for each nucleotide position in the base sequence and to display a plot of the slopes, and an $\omega_N$ module adapted to calculate $\omega_N$ for the base sequence and to display a plot of the $\omega_N$.

Another aspect of the present invention relates to a method for sequence analysis. The method comprises the steps of reading a sequence file; selecting a target sequence and a base sequence from said file; performing a non-binary comparison between the target and the base sequences, wherein the non-binary comparison generates a comparison value; and determining a similarity between the target and the base sequences based on the comparison value.

In an embodiment, the method further comprises the steps of writing aligned sequences to the sequence file and calculating an alignment percentage.

In another embodiment the method farther comprises the step of generating at least one of a two-dimensional spectral array plot or a two-dimensional single strand plot.

In another embodiment, the step of performing a non-binary comparison includes using a look-up table containing non-binary similarity score values for a plurality of possible comparisons between two sequence elements.

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

BRIEF DESCRIPTION OF THE FIGURES

FIG. 4 depicts an exemplary embodiment of a FILE MENU window in VaSSA.

FIG. 5 depicts an exemplary embodiment of a NOTEBOOK VIEWER window in VaSSA.

FIG. 6 depicts an exemplary embodiment of a SEQUENCE SUMMARY REPORT window in VaSSA.

FIG. 7 depicts an exemplary embodiment of a SEQUENCE VIEW REPORT window in VaSSA (SEQ ID NOS 2-4 disclosed respectively in order of appearance).

FIG. 8 depicts an exemplary embodiment of a SEQUENCE VIEW STATS window in VaSSA.

FIG. 12 depicts an exemplary embodiment of a QUERY REPEAT REPORT window in VaSSA (SEQ ID NO 7).

FIG. 14 depicts an exemplary embodiment of an OMEGA SUBZERO REPORT window in VaSSA.

FIG. 16 depicts an exemplary embodiment of a QUERY OMEGA REPEAT REPORT in VaSSA (SEQ ID NO 7).

FIG. 20 depicts an exemplary embodiment of a COMPARE SEQUENCE REPORT window in VaSSA.

FIG. 23 depicts a picture of a SPECTRAL ARRAY FORMULA.

FIG. 28 depicts exemplary embodiments of additional SINGLE STRAND PLOT REPORT windows in VaSSA, showing comparisons between single strand sequences.

FIG. 34A depicts a picture of the different elements involved in A\G comparison.

FIG. 34C depicts a picture of the different elements involved in A\C comparison.

DETAILED DESCRIPTION

Figure 1:
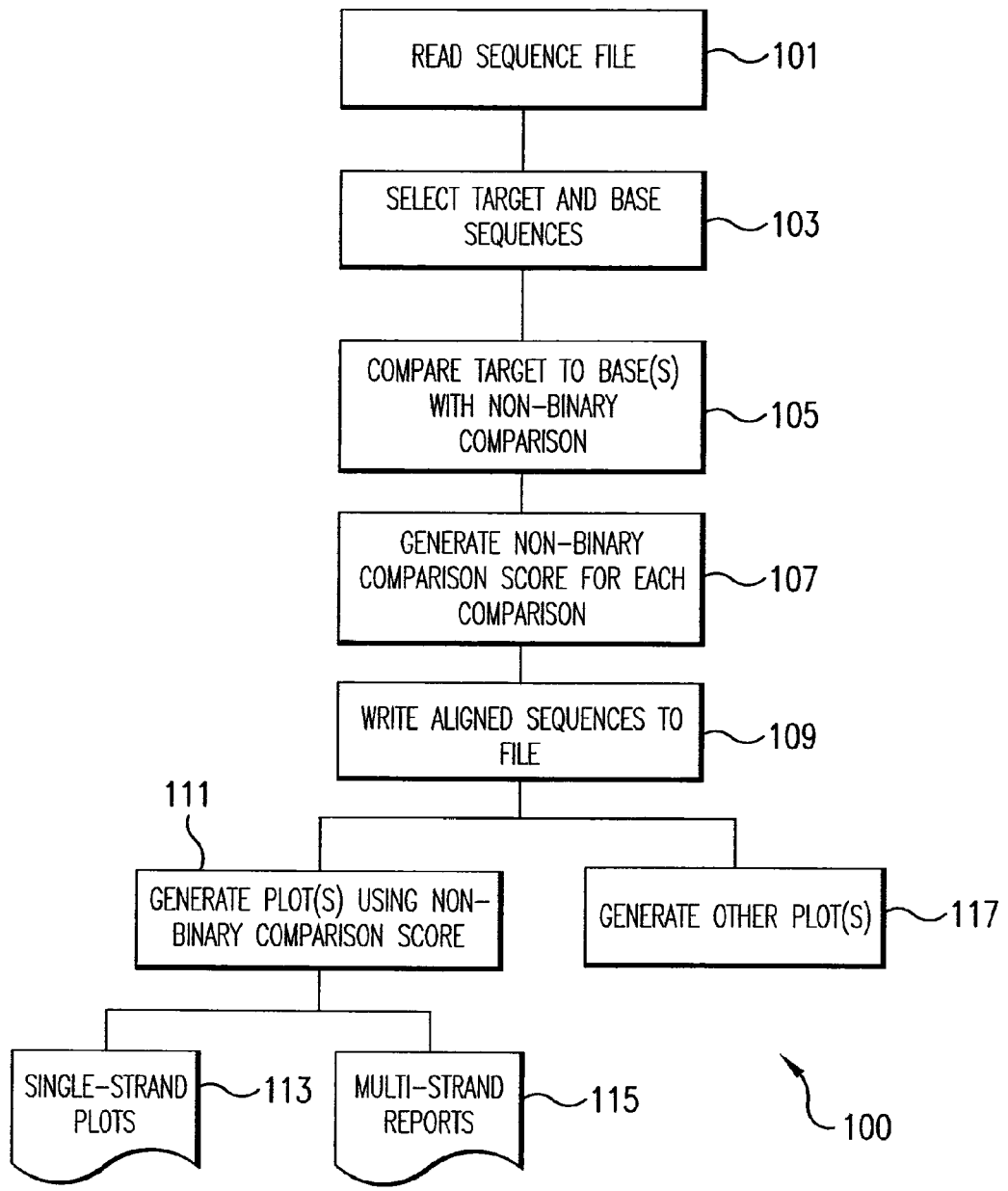
FIG. 1 depicts a flow chart of an exemplary method according to the present invention.

Embodiments of the present invention provide an integrative system for analyzing and determining sequences' structural behavior over a discrete topology space. The technology provides, among other things, new improved measurable methods, including normalization, compression technique, structural classification and topological conjugacy methods. These combinations of analytical methods take into account biology, chemistry, and computational mathematical techniques generating numerical governing properties, and/or structural behavior patterns of genomic data.

The present invention can be used in a wide range of bioinformatics applications. The integrative system and method of the present invention provide single sequence plots and other data for nucleotide sequences of essentially any length (e.g., from 50 bases to two million bases). The integrative system and method of the present invention are capable of providing comparative data for a large number of sequences due to efficient processing steps. For example, the system has been demonstrated to operate extremely fast with 500 sequences of 500 bases. Comparisons of 1000, 10,000, 100,000, 1,000,000, or more sequences are within the scope of the invention.

The system of the present invention uses a non-binary method that generates meaningful comparative information within the homology range of 0% (no identity) to 100% (complete identity). The non-binary method of the present invention is much more discriminating than typical binary comparisons and can resolve degrees of sequence difference that would be indistinguishable in a binary comparison.

The system and method of the present invention are effective in comparing sequences despite the presence of insertions or deletions of any length. An alignment module provides both global and local optimization to permit meaningful comparisons. Single strand plots and comparisons can be generated in coding (decomposable) regions and non-coding (indecomposable) regions having chaotic sequences or omega repeats.

The DNA bases (A, T, G, and C) are used in the description that follows below. However, it should be understood that the system and method of the present invention are applicable not only to DNA but to all nucleotides, including RNA (substituting Uracil for Thymine), LNA, PNA, and other synthetic nucleotide variants.

The displays shown in the figures typically depict only nucleotide sequences. As should be apparent, for coding regions, the amino acid sequence corresponding to the codons can also be displayed, using conventional techniques well known to one skilled in the art.

The method of the present invention involves analyzing, retrieving, and displaying genomic information. The system and method of the present invention provide tools for collecting, storing, analyzing, and retrieving genomic, proteomic, and medical data, data mining and data visualization and display; sequence alignment and pattern recognition; and structure prediction. For example, the system and method of the present invention can be used for predictive biochemical models, in silico assays, distributed computing, diagnosis, and design of a therapeutic plan.

The system of the present invention is composed of one or more modules. The modules and system of the present invention can be practiced by an individual operating a stand-alone computer, or as part of a distributed computing "system" operated by several individuals. The present invention also encompasses various aspects of the system, such as the hardware, software, subsystems, components of the subsystems, and structures of data produced, compiled, or assembled using the system. Furthermore, the present invention encompasses methods and equipment for gathering, producing, and displaying the relevant data, and associated analytical instrumentation, as well as methods of operating and using the instrumentation. Business methods of using the system and method of the present invention are also contemplated, such as selling subscriptions for a sequence analysis tool.

The practice of the embodiments described in further detail below will employ, unless other wise indicated, conventional methods of microbiology, molecular biology, and immunology within the skill of the art. Such techniques are explained fully in the literature. All publications, patents and patent applications cited herein, whether supra or infra, are hereby incorporated by reference in their entirety.

Definitions

In describing the present invention, the following terms will be employed, and are intended to be defined as indicated below.

"VaSSA" refers to Variation Sequence Software Application.

A "computer" refers to any apparatus that is capable of accepting a structured input processing the structured input according to prescribed rules, and producing results of the processing as output. The computer can include, for example, any apparatus that accepts data, processes the data in accordance with one or more stored software programs, generates results, and typically includes input, output, storage, arithmetic, logic, and control units. Examples of a computer include: a computer; a general purpose computer; a supercomputer; a mainframe; a super mini-computer; a mini-computer; a workstation; a micro-computer; a server; an interactive television; a web appliance; a telecommunications device with internet access; a hybrid combination of a computer and an interactive television; a portable computer; a personal digital assistant (PDA); a portable telephone; and application-specific hardware to emulate a computer and/or software, for example, a programmable gate array (PGA) or a programmed digital signal processor (DSP). A computer can be stationary or portable. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

A "machine-accessible medium" refers to any storage device used for storing data accessible by a computer. Examples of a computer-readable medium include: a magnetic hard disk; a floppy disk; an optical disk, such as a CD-ROM and a DVD; a magnetic tape; a memory chip; and a carrier wave used to carry computer-readable electronic data, such as those used in transmitting and receiving e-mail or in accessing a network.

"Software" refers to prescribed rules to operate a computer. Examples of software include: software; code segments; instructions; software programs; computer programs; and programmed logic.

A "computer system" refers to a system having a computer, where the computer comprises a computer-readable medium embodying software to operate the computer.

An "information storage device" refers to an article of manufacture used to store information. An information storage device has different forms, for example, paper form and electronic form. In paper form, the information storage device includes paper printed with the information. In electronic form, the information storage device includes a computer-readable medium storing the information as software, for example, as data.

The following terms are not in the standard glossary of genetics and bioinformatics.

A "string" is a sequence of characters. A sequence may be considered as a n×1 matrix known as an n-tuple of objects (characters). In the case of nucleotide sequences, e.g. DNA, RNA, or synthetic or other variants, each nucleotide element has a unique position in the string which is a discrete set.

Example: AGCAATATAGGA (SEQ ID NO 1) is a string of characters whose length is 12.

A "subsequence" of a string S means a sequence of characters of S that need not be consecutive in S, but do retain their order as given in S.

Example: ACG is a subsequence of ACTCGT.

"$f(n)=O(g(n))$": Let $f(n)$ and $g(n)$ be functions. Then $f(n)=O(g(n))$ if and only if there is a constant c such that, for all n sufficiently large $|f(n)| \leq cg(n)$.

"$S_4$" is the DNA sequence set on the four Nucleotides: A, C, G, and T.

$\sigma_L: S_4 \to S_4$ given by $\sigma_{k,L}(s_0 s_1 s_2 \bullet\bullet\bullet s_n \bullet\bullet\bullet) = s_0 \underline{s_1 s_2 \bullet\bullet\bullet s_n \bullet\bullet\bullet}$ where k=1 (which represents shifting by 1) and the L represents moving from left to right. Thus $\sigma_L$ is a continuous DNA valued function defined on $S_4$. One way to visualize the map is that it simply "forgets" the first entry in a sequence and focuses on all other entries to the right (i.e., the underlined portion of the sequence above). The intuitive notion of this DNA continuity can be described by stating that the asymptotic linguistic variation above on a small neighborhood of any position DNA subsequence in $S_4$ will vary only slightly from that position. This variation can be made as small or as large as one would like it to be by decreasing or increasing the size of neighborhood.

$\sigma_{t,R}$ is an analog map to the above that is shifting to the left by t units and reading from the right. The continuity of these maps allows the maps to be combined.

Forward and backward orbit of a subsequence: The forward orbit of a subsequence z is the set of points z, $\sigma_L(z), \sigma_L^2(z), \sigma_L^3(z)$, $\bullet\bullet\bullet$ and is denoted by $O^+(z)$. The backward orbit of a subsequence z is the set of points z, $\sigma_R(z), \sigma_R^2(z), \sigma_R^3(z)$, $\bullet\bullet\bullet$, and is denoted by $O^-(z)$.

Fixed and periodic subsequence: The DNA subsequence s is a fixed subsequence for $\sigma_L$ if $\sigma_L(s)=s$. The DNA subsequence s is a periodic subsequence of period n, if $\sigma^n_L(s)=s$. The least positive n is called the prime period of s. The set of all iterates of a periodic point form a periodic orbit.

Eventually periodic: A DNA subsequence s is eventually periodic of period n, if s is not periodic but there exists m>0 such that $\sigma_L^{n+i}(s) = \sigma^i(s)$ for every t≧m. That is $\sigma_L^i(s)$ is periodic for t≧m.

Forward asymptotic: Let s be a DNA subsequence which is periodic of period n. A subsequence x is forward asymptotic to s, if $$\lim_{i \to \infty} \sigma_L^{in}(s) = s.$$

The stable set of s denoted by $S^s(s)$ consists of all subsequences forward asymptotic to s.

"Aligner" is a version of multiple sequence alignment analysis.

"Omega Comparator" is the single and multiple sequence base search base on the $\omega_o$ measure.

"Spectral Array" is a series of calculations which allows one to compare all nucleotides in multiple strings which generates its unique structure with respect to the $\omega_o$ measure that enables one to find the optimal linguistic behavior.

"DNA $\omega_o$ Genetic Code Viewer" is a finer classification of the genetic code with the measure $\omega_o$.

"Stable Analytical Profiler" is a technique that defines a set of all subsequences forward asymptotic to a target subsequence.

"Unstable Analytical Profiler" is a technique that defines a set of all subsequences backward asymptotic to a target subsequence.

Chaotic: $\sigma_L(z)$ is said to be chaotic if, (1) $\sigma_L(z)$ has a sensitive dependence with respect to a target subsequence; (2) $\sigma_L(z)$ is topological transitive; and (3) the periodic subsequences are dense with respect to a string or a data set.

"Symbolic DNA Orbit" is the asymptotic symbolic behavior of a target subsequence in a sequence in an iterative process.

"Analytical DNA Orbit" is the asymptotic linguistic behavior of a target subsequence in a sequence.

"DNA Approximate Analysis" is a series of techniques which give precise structural behavior to low complexity subsequences.

"Chaotic Region Classification" is a technique which uniquely partitions subsequence targets in three categories: (1) targets sensitively dependent on initial conditions, (2) targets that are topologically transitive, and (3) periodic subsequence that are dense in their DNA sequence.

The "DNA Derivative" is a measurement which enables one to observe change qualitatively from one nucleotide to the next in a DNA sequence.

The "DNA Bifurcation" is a technique which observes the change in subsequence under different parameters.

"DNA Topological Conjugate" is a technique which shows when different mappings of σL(z) are completely equivalent.

"Confidence Score" is a measure which classifies a family of sequences from closest to farthest to a target sequence. The omega similarity score, or $\omega_o$ measure, is defined as $$\omega_0(s,t) = \frac{\sum_{i=0}^{N} s_i/t_i}{16*N},$$

wherein $s_i/t_i$ is a non-binary function, examples of which are defined in Table 1 and 2, and N is the number of nucleotides in the shorter of the two sequences being compared. The omega similarity score is a non-binary comparison of any two nucleotide strings, s and t, at base position i, with the value of the comparison given in a look-up table.

Embodiments of the present invention are discussed in detail below. While specific exemplary embodiments are discussed, it should be understood that this is done for illustration purposes only. A person skilled in the relevant art will recognize that other components and configurations can be used without parting from the spirit and scope of the invention.

FIG. 1 is an exemplary embodiment. The method 100 of the present invention may include the steps of: reading a sequence file (101); selecting a target sequence and a base sequence from the file (103); comparing the target sequence to the base sequence(s) using a non-binary comparison (105) and generating a similarity score (107); and writing aligned sequences to the file (109). Optionally, the method 100 may further include the steps of generating visual representations of the comparisons (111), calculating an alignment percentage; and/or generating a two-dimensional single strand plot or spectral array plot (113), a multi-strand report (115) or other plot (117).

A sequence file may be a machine-readable file containing one or more genetic sequences. There are a variety of acceptable formats for DNA sequences. The EMBL format is acceptable. A sequence file in this format may contain several sequences. One sequence entry starts with an identifier line ("ID"), followed by further annotation lines. The start of the sequence may be marked by a line starting "SQ" and the end of the sequence may be marked by two slashes ("//"). FASTA format is also acceptable. A sequence in FASTA format begins with a single-line description, followed by lines of sequence data. The description line must begin with a greater-than (">") symbol in the first column. Many other formats such as GCG, GenBank, and IG may also be accepted.

The sequence data may be in text form, e.g., ASCII, or some other representation readable by a computer executing the method of the invention. Reading the sequence file may include directly typing sequences in, reading from a disk, or accessing the public domain using a well-known interface such as Entrez. The files can be stored and analyzed, or analyzed "on the fly". The user may choose to read a single file or multiple files, or the whole data base, or any subsequence of any length in a file or multiple files, or the whole data base.

A target is a subsequence of any length. A user may choose to perform an analysis on a database, or on a file which enables him to observe the structural behavior. The targets are distinguished from each other in two steps. The first biological connection is the alphabets that makeup the subsequence target. The second connection is the omega zero biological connection.

In one embodiment, the step of generating the spectral array plot comprises the steps of calculating $\omega_N$; performing a radial comparison; extracting alignment coefficients; and plotting the alignment coefficients.

In another embodiment, the step of generating the spectral array plot further comprises the steps of reversing one of the base or the target; and reversing a mod.

In another embodiment, the step of performing a non-binary comparison includes the step of using a look-up table containing non-binary similarity score values for a plurality of possible comparisons between two sequence elements.

In yet another embodiment, the method of the present invention contains the steps of comparing a molecular structure of a first nucleotide to a second nucleotide; determining a first non-binary similarity score based on said comparison; populating a look-up table with the similarity scores for each nucleotide; and using the look-up table to calculate a second non-binary similarity score that compares a target sequence (t) of nucleotides to a base sequence (s) of nucleotides.

Figure 38:
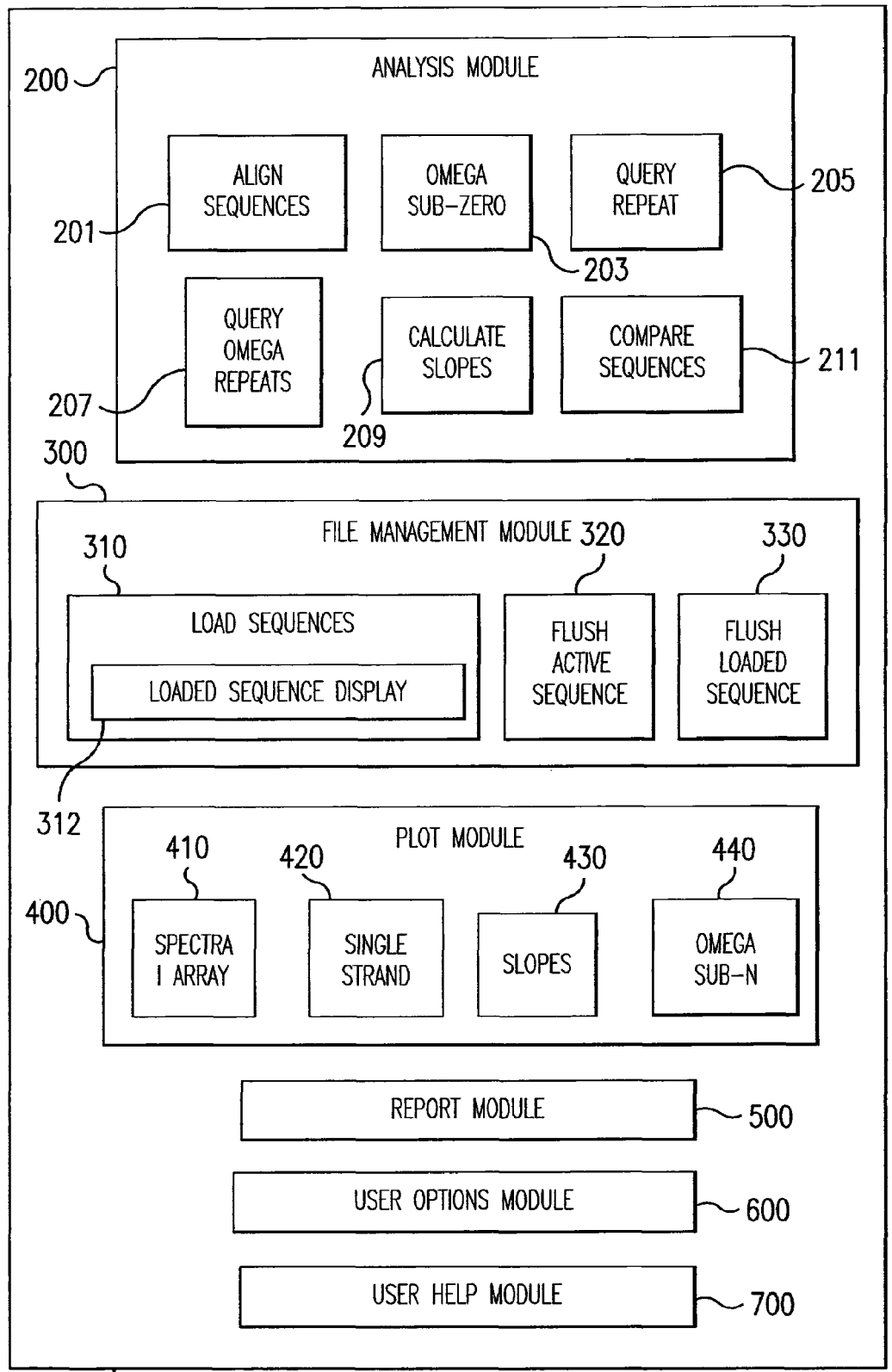
FIG. 38 depicts an exemplary embodiment of the non-binary sequence comparison system according to the present invention.

FIG. 38 depicts an embodiment of the non-binary sequence comparison system 10 of the present invention. The system 10 comprises an analysis module 200, adapted to calculate a non-binary similarity score between a first nucleotide sequence and a second nucleotide sequence, a file management module 300, a plot module 400 and, optionally, a report module 500, a user options module 600, and/or a user help module 700.

The file management module 300 of the non-binary sequence comparison system 10 manages sequence files. In one embodiment, the file management module 300 comprises a load sequences module 310, adapted to load at least one sequence file; a flush active sequence module 320, adapted to flush a sequence file from a memory; and a flush loaded sequence module 330, adapted to flush a loaded sequence file from the memory. In another embodiment, the load sequence module 310 comprises a loaded sequence display module 312, adapted to generate and display a summary report notebook page when a sequence is loaded. The summary report notebook page is adapted to display a sequence file name and a number of sequences.

In another embodiment, the plots module 400 of the non-binary sequence comparison system 10 comprises a spectral array module 410, adapted to plot aligning coefficients for a base sequence and a target sequence; a single strand module 420 adapted to plot a single strand for the base sequence and the target sequence; a slopes module 430 adapted to calculate a slope for each nucleotide position in the base sequence and to display a plot of the slopes, and an $\omega_N$ module 440 adapted to calculate $\omega_N$ for the base sequence and to display a plot of the $\omega_N$. In a preferred embodiment, the spectral array module 410 is further adapted to calculating an $\omega_N$ value for radial compare and extracting aligning coefficients. In another preferred embodiment, the single strand module 420 is adapted to calculate an $\omega_N$ value for the base sequence and the target sequence.

In another embodiment, the report module 500 of the non-binary sequence comparison system 10 of the present invention is adapted to generate and display a sequence summary, a listing of the contents of each loaded sequence, and/or statistical information about each loaded sequence.

In yet another embodiment, the analysis module 200 of the non-binary sequence comparison system 10 comprises an align sequences module 201, adapted to align a target sequence to a base sequence and to display an alignment report; an $\omega_0$ module 203, adapted to calculate an $\omega_0$ score for a sequence and to display the $\omega_0$ score; a query repeat module 205, adapted to locate multiple occurrences of the target sequence in the base sequence and to display the multiple occurrences; a query omega repeats module 207, adapted to determine when repeated nucleotides are duplicates; a calculate slopes module 209, adapted to calculate a slope for each nucleotide position in the base sequence and to display a slopes report; and a compare sequences module 211, adapted to compare the target sequence to the base sequence and to display a similarity report.

In a preferred embodiment, the align sequences module 201 is further adapted to perform the action of reversing said base sequence, reversing a mod, aligning the base and the target to a shortest length, calculating an alignment percentage, and/or calculating an omega similarity score.

In another preferred embodiment, the compare sequences module 211 is further adapted to perform the action of reversing the base sequence, reversing the target sequence, reversing a mod, calculating an $\omega_N$ value for each of the base and the target sequences, converting the base and the target sequences to binary, calculating a distance between the base sequence and the target sequence, and determining if the distance exceeds a bound.

Figure 2:
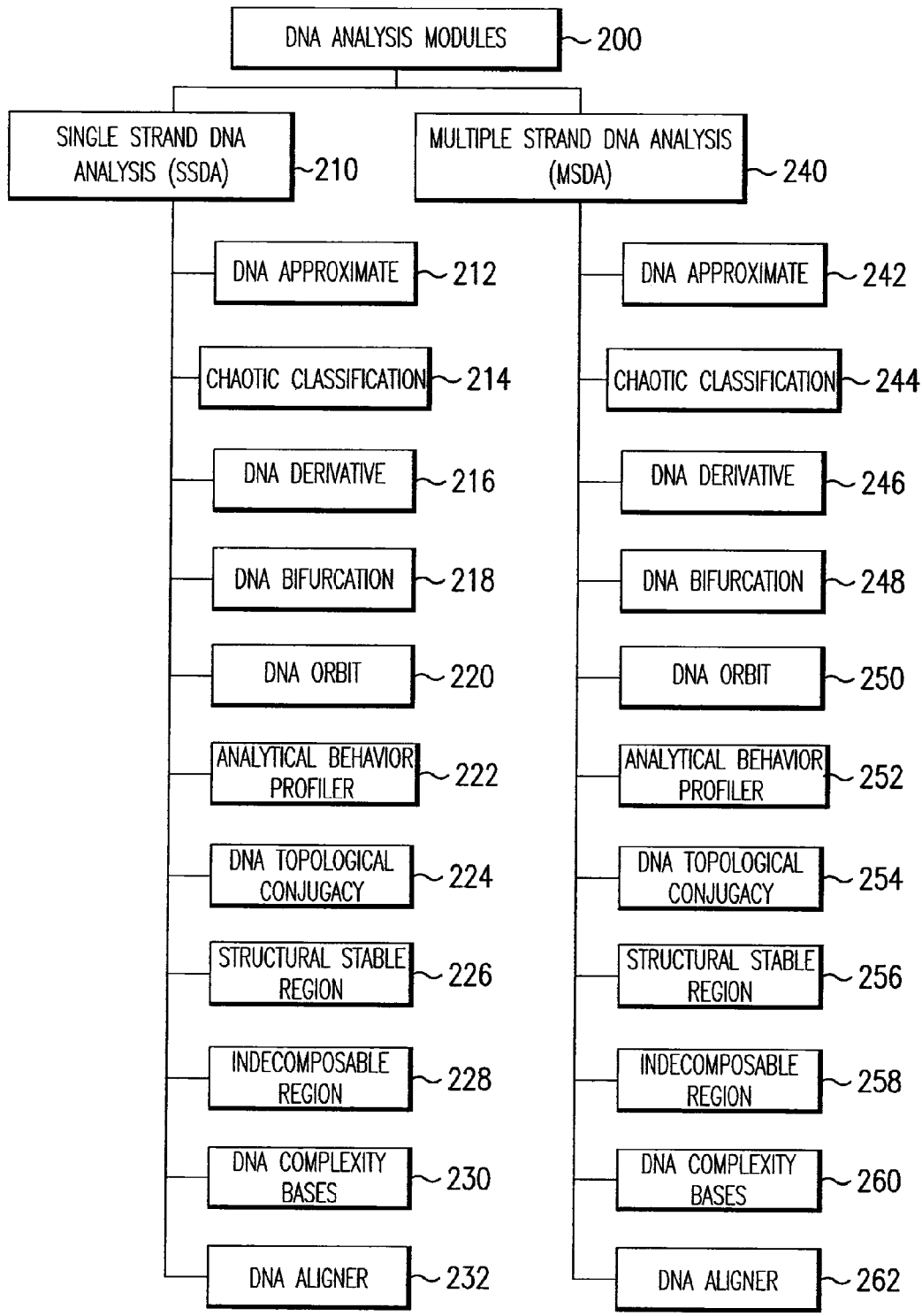
FIG. 2 depicts an exemplary embodiment of sub-modules of the DNA Analysis modules according to the present invention.

FIG. 2 depicts a layout of a preferred module decomposition of the DNA analysis portion of the VaSSA architecture. The modules in the decomposition are discussed in more detail below. Submodules are depicted in flowchart form in FIGS. 35 to 38.

Module Decomposition of VaSSA Architecture

DNA Analysis Module groups 200
   SSDA (Single Strand DNA Analysis) module group 210
   MSDA (Multi-Strand DNA Analysis) module group 240

SSDA (Single Strand DNA Analysis) (FIG. 2)
   DNA Approximate Module 212
   Chaotic Region Classification Module 214
   The DNA Derivative Module 216
   The DNA Bifurcation Module 218
   DNA Orbit Module 220
   Analytical Behavior Profiler Module 222
   DNA Topological Conjugacy Module 224
   Structural Stable Region Module 226
   Indecomposable Region Module 228
   DNA Complexity Bases Module 230
   DNA Aligner Module 232

MSDA (Multi-Strand DNA Analysis) (FIG. 2)
   DNA Approximate Module 242
   Chaotic Region Classification Module 244
   The DNA Derivative Module 246
   The DNA Bifurcation Module 248
   DNA Orbit Module 250
   Analytical Behavior Profiler Module 252
   DNA Topological Conjugacy Module 254
   Structural Stable Region Module 256
   Indecomposable Region Module 258
   DNA Complexity Bases Module 260
   DNA Aligner Module 262

DNA Topological Conjugacy Module 224 and 254 (FIG. 35)
   a. Analytical Profiler Module 3501
   b. Analytical Mapper Module (Creation of Analytical Mapping) 3503
   c. Conjugacy Comparison Module 3505
   d. First Iteration Analysis Module 3507
   e. Phase Portrait Generator Module 3511

DNA Approximate Module 212 and 242 (FIG. 36)
   a. Holomorphic Form Generator Module 3601
   b. Approximate Constructor Module 3603
   c. P & Q Coefficient Calculator Module 3605
   d. JC-DNA Curve Generator Module 3607
   e. Low Complexity Generator Module 3609
   f. Target Classifier Module 3611
   g. Symbolic DNA Orbit Module (also a child of SSDA and MSDA) 3613
   h. Analytical DNA Orbit Module (also a child of SSA and MSDA) 3615

DNA Orbit 220 and 250 (Analytical DNA Orbit Module)
   Symbolic DNA Orbit Module 3701
      a. Symbolic Flow Generator Module 3703
      b. Row Difference Generator Module 3705
      c. Orbit Generator Module 3707
   Analytical DNA Orbit Module 3709
      a. Analytical Forward Profiler Module 3711
      b. Analytical Backward Profiler Module 3713
      c. DNA Attractor Generator Module 3715
      d. DNA Repeller Generator Module 3717

Chaotic Region Classification Module 214 and 244
   Chaotic Region Classifier 3801
      a. DNA Sensitivity Generator Module 3803
      b. DNA Transitivity Generator Module 3805
      c. Dense Periodic Sequence Generator Module 3807

The DNA Bifurcation Module 218 and 248
   Splitter Classifier 3901
      a. DNA Transitivity Splitter Profiler Module 3903
      b. DNA Dense Splitter Profiler Module 3905

The DNA Derivative Module 216 and 246
   Derivative Generator Module 4001
   Monotonic Generator Module 4003
      a. Positive Measure Module 4005
      b. Negative Measure Module 4007

Analytical Behavior Profiler Module 222 and 252
   DNA Approximate Module 4101
   Chaotic Region Classification Module 4103
   The DNA Derivative Module 4105
   The DNA Bifurcation Module 4107
   DNA Orbit Module 4109
   Analytical Behavior Profiler Module 4111
   DNA Topological Conjugacy Module 4113
   Structural Stable Region Module 4115
   Indecomposable Region Module 4117
   DNA Complexity Bases Module 4119
   DNA Aligner Module 4121
   Algebraic Structure Generator Module 4123
      a. Group Generator Module 4125
      b. Semi-Group Generator Module 4127
      c. Ring Generator Module 4129
      d. Analytical Set Generator Module 4131
   Homomorphism-Generator Module 4133
   Isomorphism-Generator Module 4135

Structural Stable Region Module 226 and 256
   Repeat Generator Module 4201
   Forward Asymptotic Module 4203
   Stability Profiler Module 4205

Indecomposable Region Module 228 and 258
   DNA Orbit Analysis Module 4301
   Non-repeat Generator Module 4303
   Indecomposable Profiler Module 4305

DNA Complexity Bases Module 230 and 260
   Repeat Generator Module 4401
   Universal DNA Basis Generator Module 4403
   Density Generator Module 4405

DNA Aligner Module 232 and 262
   Symbolic Aligner Module 4501
      a. Single Strand Generator Module 4503
      b. Multi-Single Strand Generator Module 4505
   Omega Comparison Aligner Module 4507
      a. Omega Single Strand Generator Module 4509
      b. Multi-Single Strand Generator Module 4511

Descriptions of Main Modules of VaSSA

DNA Approximate Module 212 or 242: This module reduces the polynomial type construction that is in VaSSA. It shows that not all the coefficients off are needed to perform a calculation. Also, the approximant generates data that can be used for visualization of the linguistic structure behavior of low complexity subsequences. This procedure is performed without losing any biological information. The approximant is at a lesser order which provides a faster, more precise analysis and the calculation gives a better fitting of the original function.

Chaotic Region Classification Module 214 or 244: This module possesses three ingredients: unpredictability, elements of regularity, and elements that cannot be broken down to smaller subsequences.

DNA Derivative Module 216 or 246: This module creates an environment where monotonic changes in content can be observed as a DNA string is read from left to right and/or from right to left. When the DNA derivative is positive, the information being transferred is increasing. When DNA derivative is negative, the information being transferred is decreasing. When the DNA derivative is zero, the information being transferred is constant.

DNA Bifurcation Module 218 or 248: This module analyzes the changes in the DNA maps as they undergo parameter changes. These changes often involve the periodic subsequences of DNA but also involve other changes as well.

DNA Orbit Module 220 or 250: Even though analysis of DNA sequences is mathematical in nature, this module creates an environment which answers the somewhat nonmathematical question: where do subsequences go and what do they do when they get there? This module connotes the geometric process of taking one subsequence to another assuming that DNA sequences are discrete sets.

Analytical Behavior Profiler Module 222 or 252: This module takes into account all of its children modules and then connects them through algebraic functional methods which does not lose the content of the biology. It then further refines information by dissecting the dynamic information from the child modules to algebraic equivalence classes.

DNA Topological Conjugacy Module 224 or 254: This module relates data sets to data sets, DNA sequences to DNA sequences, and multiple DNA sequences to DNA sequences. It creates an environment which classifies sequences that are completely equivalent and not equivalent.

Structural Stable Region Module 226 or 256: This module relates to understanding all orbits, and to identifying the set of orbits which are periodic, eventually periodic asymptotic, etc. Implementation of qualitative and/or geometric techniques to understand a given data set.

Indecomposable Region Module 228 or 258: This module relates to understanding all non-orbits, and to identify the set of non-orbits which are not periodic, eventually periodic or asymptotic, etc. Implementation of qualitative and/or geometric techniques to understand a given data set.

DNA Complexity Bases Module 230 or 260: This module creates a universal DNA set in which observations of how non-periodic subsequences are arbitrarily close to another sequence can be made. The module creates an environment where linguistic behavior agrees in a large number of places, which create linguistically dense orbits. These orbits are called topologically transitive.

DNA Aligner Module 232 or 262: This module is VaSSA's version of a system of tool kits analyzing sequence alignment. In addition, the module may be enhanced with additional biological information modules such as symbolic DNA orbit, etc.

FIG. 3-FIG. 28 depict exemplary embodiments of a graphical user interface (GUI) with the VaSSA, during VaSSA execution.

The aligned sequences may then be written back to the sequence file, or a different file. The percentage of alignment may then be calculated, which shows the percentage of the two sequences that are in alignment.

An omega similarity score (which is $\omega_o$) may also be calculated. The algebraic structure of $\omega_o$ is defined as $$\omega_0(s, t) = \frac{\sum_{i=0}^{N} s_i/t_i}{16*N}.$$

The omega similarity score, or $\omega_o$ measure, is a non-binary comparison of any two nucleotide strings, s and t. This can easily be modified for analysis on a single string by substituting $s_i/t_{i+1}$ for $s_i/t_i$ in the foregoing equation.

Figure 33:
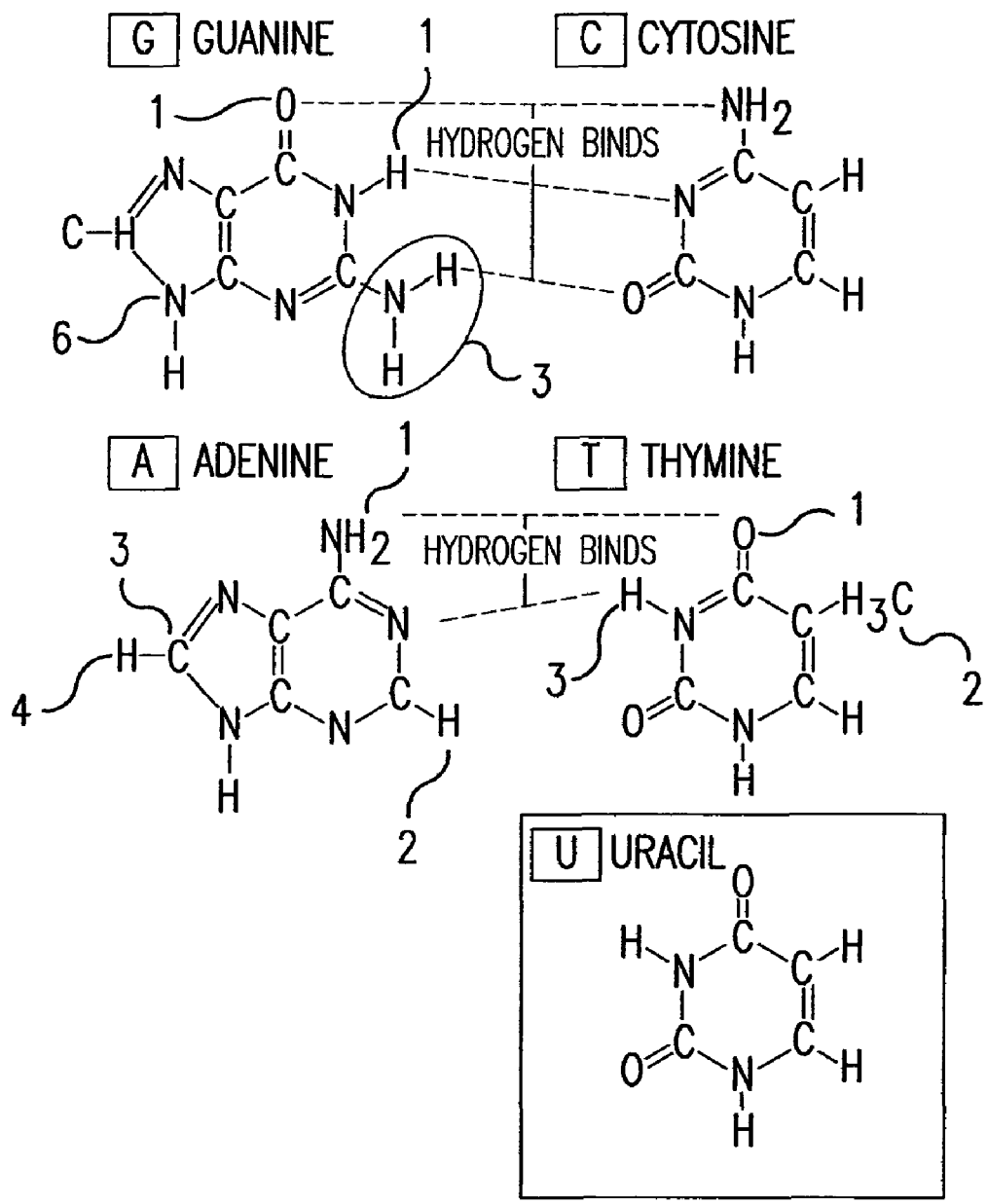
FIG. 33 depicts the chemical structure of the four bases of nucleic acids guanine, cytosine, adenine, and thymine, and uracil, which replaces thymine in RNA

The omega similarity score may be calculated in several ways. The value of the $s_i/t_i$ comparison is based on the chemical structure of the nucleotides of DNA. In DNA, there are four possible bases: adenine (A), cytosine (C), guanine (G), and thymine (T). In RNA, the thymine is replaced by uracil (U). The structure of these bases is shown in FIG. 33. The purines, adenine and guanine, have a two ring structure, and the pyrimidines, cytosine, thymine and uracil, have a single ring structure. The value $s_i/t_i$ represents the differences in structure between the various bases. In the purine base structure, there are two rings, which can be considered the large, six-membered ring and the small, five-membered ring. The pyrimidine structures have only one ring. The measurement can be broken down into four categories: purine\purine, pyrimidine\pyrimidine, purine\pyrimidine and pyrimidine\purine.

Traditional methods of comparing DNA sequences operate by comparing the base sequences in a binary fashion, i.e., simply assessing whether the base is the same or different. In one aspect, the present invention is a method of comparing DNA sequences that takes into account not only that bases are different, but measures the magnitude of the difference. Thus, the invention includes a non-binary method of comparing DNA sequences.

In a first embodiment, steric considerations are primarily considered. In this embodiment, a value of 0 is assigned if the bases are identical, 1 is assigned for purine\purine, pyrimidine\pyrimidine arrangements, i.e. where the bases are the different but the ring size is unchanged, and 2 is assigned for purine\pyrimidine and pyrimidine\purine, where the ring size of the base changes. Thus, $\omega_o$ reflects not only a difference in the identity of the base, but also the degree of differences between the chemical structure of the purines and the pyrimidines.

The first embodiment is illustrated in Table 1:

TABLE 1

|  |  | S |  |  |  |
|---|---|---|---|---|---|
|  | s/t | A | G | C | T |
| T | A | 0 | 1 | 2 | 2 |
|  | G | 1 | 0 | 2 | 2 |
|  | C | 2 | 2 | 0 | 1 |
|  | T | 2 | 2 | 1 | 0 |

A second embodiment of the invention further considers the number of elements in the base $s_i$ not present in the base $t_i$ in the respective position of the molecular structure. A purine\purine measurement compares both the large ring and the small ring. This is where the molecular arrangement is most similar and both purine molecules behave similarly with respect to size and arrangement of their chemical elements. The measurement, referred to herein as $\omega_0$, is calculated in one embodiment by counting the number of atoms present in the first sequence that are not present in the second sequence. For example, if a first sequence s has a guanine ("G") nucleotide at position i and the second sequence t has an adenine ("A") nucleotide at the corresponding position, there then $\omega_0$ measure at position i (referred to herein as $s_i/t_i$) is calculated by determining the number of atoms in si not present and/or in a different position in $t_i$. Referring now to FIG. 33, in the guanine molecule, the oxygen atom (1), the hydrogen atom (2) and the NH2 group of atoms (3, 4, 5) bonded to the large ring, and the hydrogen (6) and carbon (7) atoms in the small ring opposite the double bonded carbon atoms are either not present or in a different position in the adenine molecule. Accordingly, $s_i/t_i=7$ where $s_i=G$ and $t_i=A$. Thus, $\omega_0$ reflects the degree of differences and similarities in chemical structure of the purines. It is assumed that these differences and similarities have biological significance in coding and non-coding regions of the nucleotide sequence. The calculation of $\omega_0$ may be modified with more precise information at the bonding level for each chemical element in other embodiments.

In the calculation of the omega measure, when the omega measure is identically zero, the chemistry is identically the same. Where the omega measure is not identically zero, the omega measure gives a number which represents the number of different chemical elements. A complete analysis on the four nucleotides is displayed in the Table 2 below. The $s_i/t_i$ value in a pyrimidine\pyrimidine analysis is carried out in an analogous fashion as the purine\purine measure, except only the single ring is considered. In a purine\pyrimidine or pyrimidine\purine measurement, the large ring of the purine is compared to the ring of the pyrimidine but the comparison is performed counterclockwise on the large ring of the purine and clockwise on the pyrimidine ring (or vice-versa). The structures of the molecules are shown in FIG. 33. However, the measure value does not change since the structure of the nucleotide elements structure does with respect to two ring verses one ring, etc.

Using this second embodiment of the invention, a matrix can be generated to determine values of $s_i/t_i$, as seen in Table 2:

TABLE 2

|  |  | S |  |  |  |
|---|---|---|---|---|---|
|  | s/t | A | G | C | T |
| T | A | 0 | 7 | 4 | 9 |
|  | G | 6 | 0 | 7 | 7 |
|  | C | 6 | 10 | 0 | 6 |
|  | T | 9 | 8 | 4 | 0 |

Figure 34B:
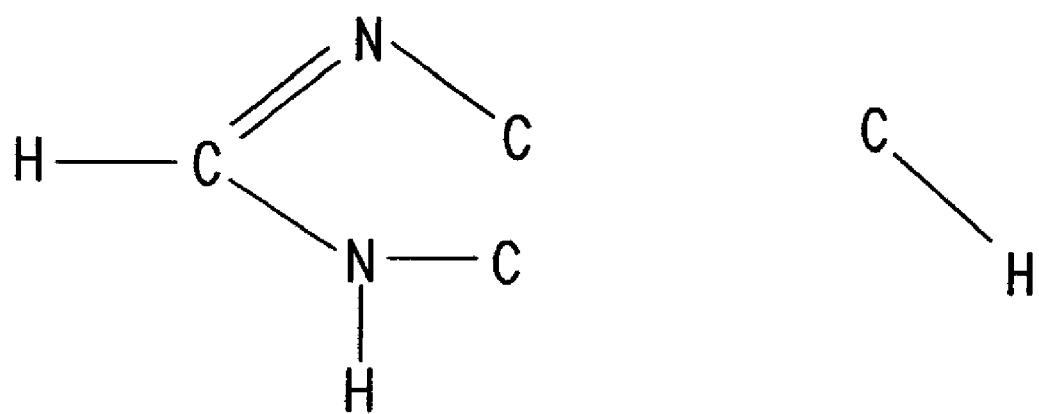
FIG. 34B depicts a picture of the different elements involved in G\A comparison.
Figure 35:
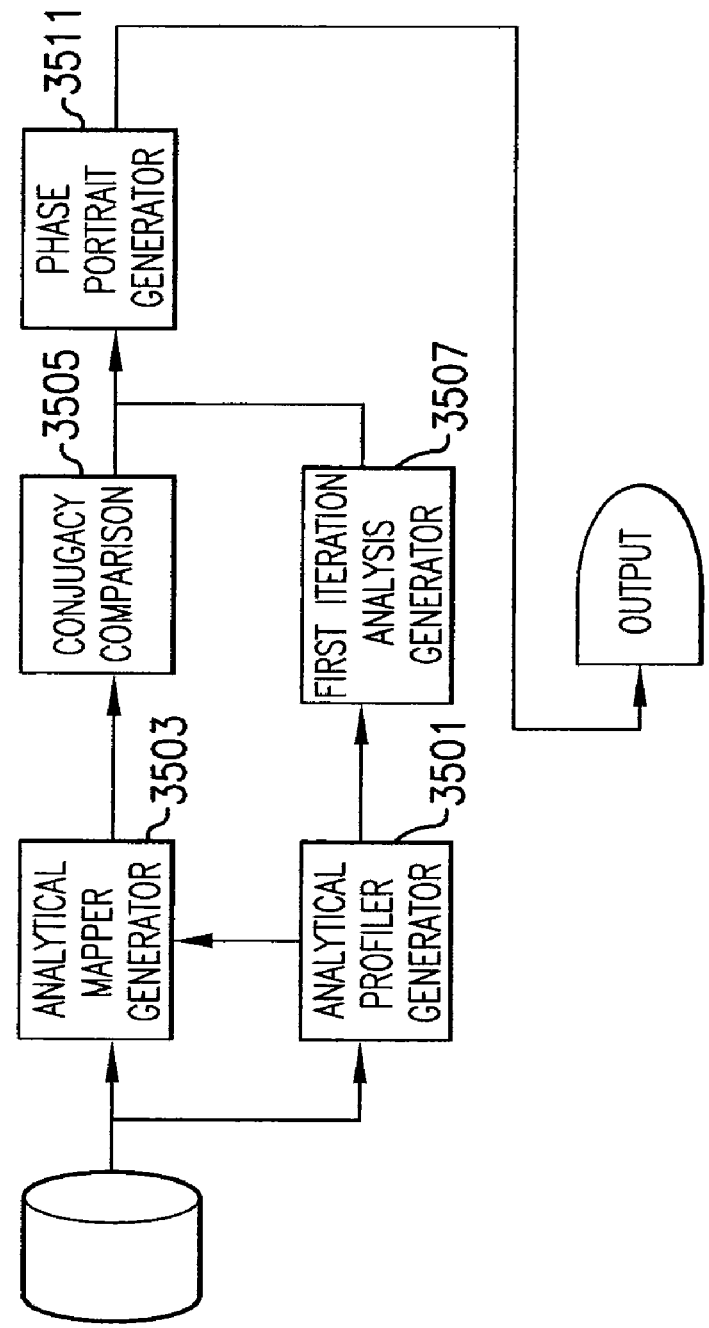
FIG. 35 depicts an exemplary embodiment of the DNA topological conjugacy module according to the present invention.
Figure 36:
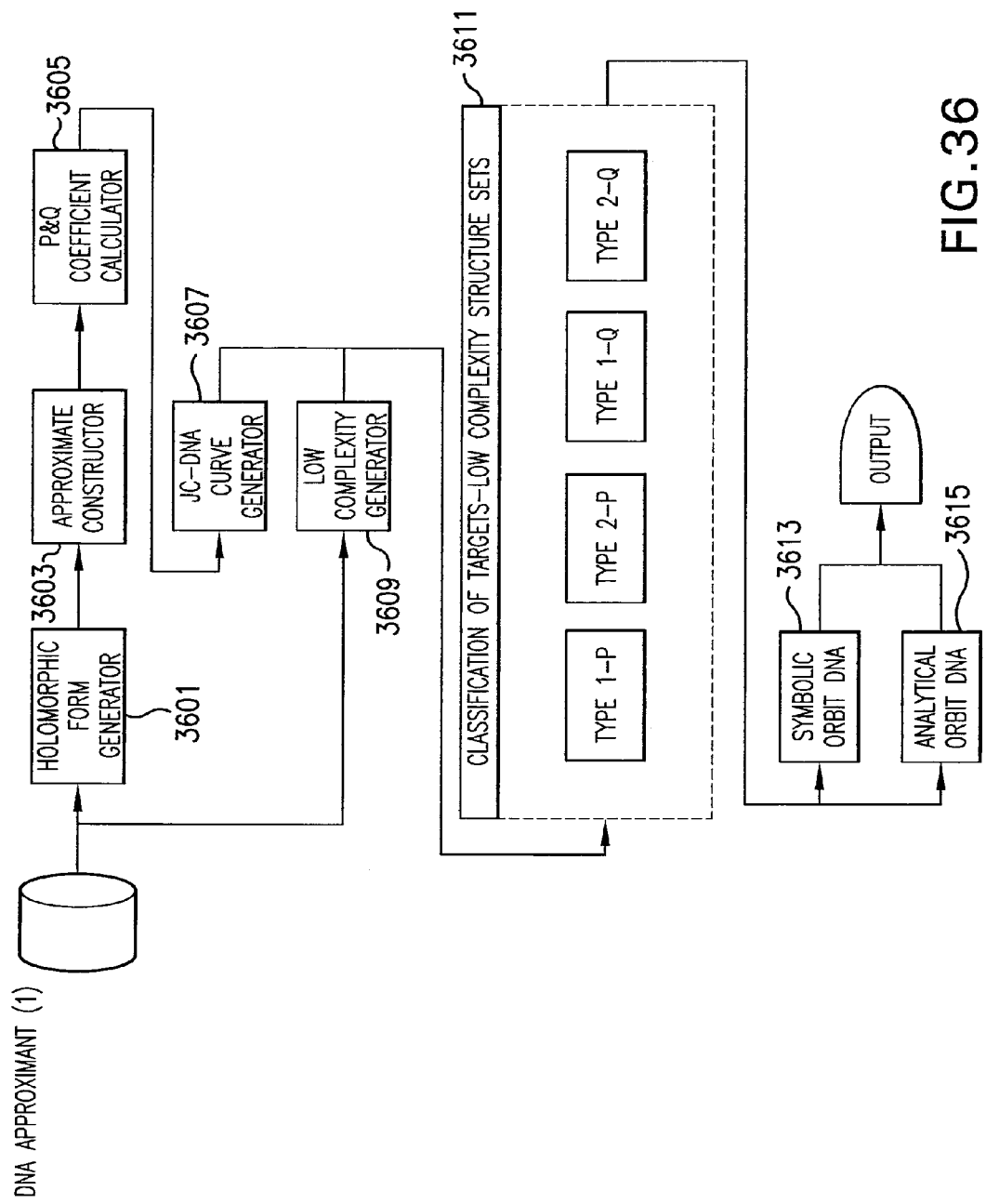
FIG. 36 depicts an exemplary embodiment of the DNA approximate module according to the present invention.
Figure 37:
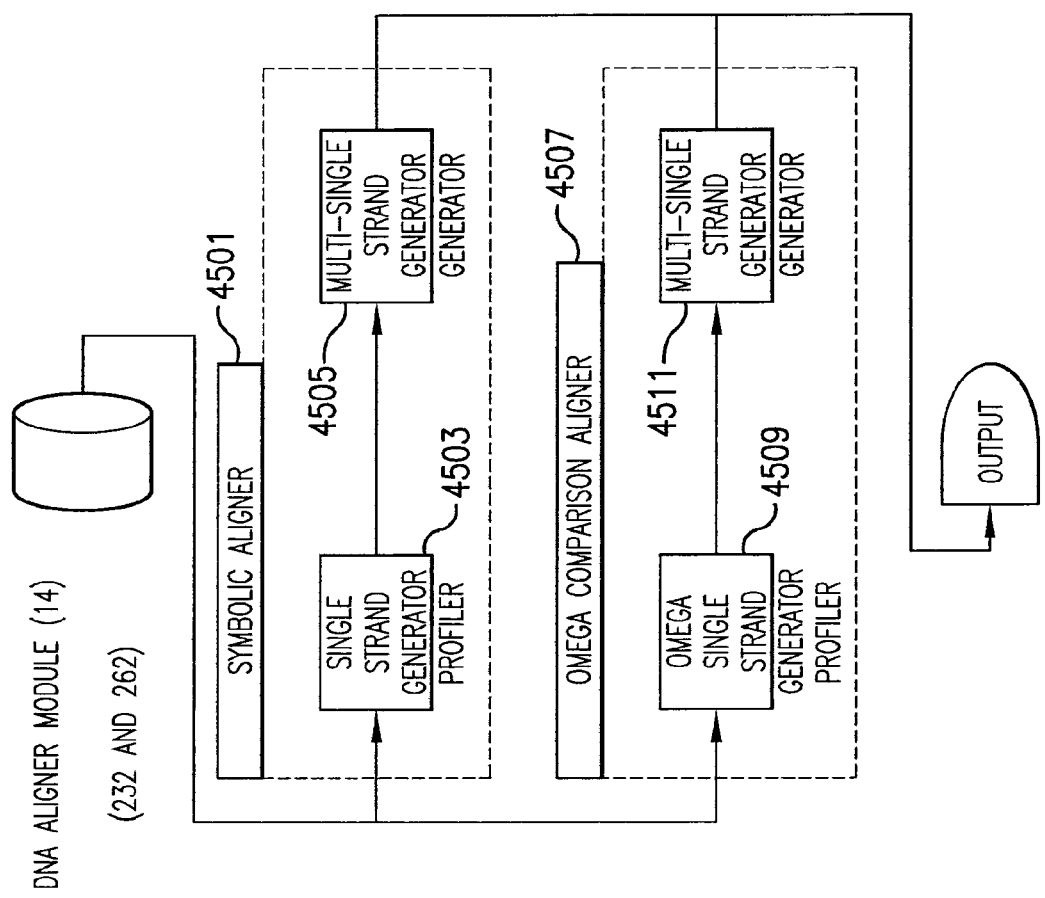
FIG. 37 depicts an exemplary embodiment of the DNA aligner module according to the present invention.

FIGS. 34A-34C display some examples of the result of the omega count and the chemical elements involved. The figures demonstrate graphically why A/G is more similar than A/C and A/T, and G/A is more similar than G/C and G/T, and so on. Even though the omega measure generates numbers for G/A and G/T that are the same, the chemical elements involved are different. The redundancy of the elements of the table is clarified by the figures, which depict the elements involved. The real-world significance of these similarities or differences is to be able to describe how similar or how different a set of sequences is, without losing the integrity of traditional biological relevance in present sequence alignment searches. Other difference matrices can be used based on other chemical comparisons between the bases.

In view of the present disclosure, persons skilled in the art will be able to construct corresponding tables for RNA and protein In one embodiment, two alternative sequences t and r:
t=AAGCC
r=AAGAC
are compared to a native sequence s:
s=ATAGC It is observed that r and t differ from s by three bases. However, r and s are not identical, and the question to be considered is: which of r and t is more similar to s?

Using a traditional approach, one can define a quantity $S(s,t)$ and $S(s,r)$ to compare t and r, respectively, to s. Using the common BLAST system, wherein $S(x_i, y_j)=s(x_iy_j)=\{+1, x_i=y_j, -\mu, x_i \neq y_j$ and $$S(x, y) = \sum_{i,j}^{n,m} s(x_i, y_j),$$

where $\mu$ is a constant, the similarity scores for s and t are:
$S(s,t)=2-3\mu$
$S(s,r)=2-3\mu$
No apparent difference is observed.

Using the first embodiment of the invention as described above in connection with Table 1, values of $\omega_0(s,r)$ and $\omega_0(s,t)$ are determined as follows:

$\omega_0(s,r)=(0+2+1+1+0)=4$ $\omega_0(s,t)=(0+2+1+2+0)=5.$

Thus, we see that there is a difference.

Using the second embodiment of the invention as described above, values of $\omega_0(s,r)$ and $\omega_0(s,t)$ are determined using (wherein N represents the length of the shorter of the two sequences being compared):

$$\omega_0(s, t) = \frac{\sum_{i=0}^{N} s_i / t_i}{16 * N} \quad (1)$$

as follows:

$$\omega_0(s, r) = \frac{(0+9+6+7+0)}{80} = 22/80 = 0.275$$

$$\omega_0(s, t) = \frac{(0+9+6+10+0)}{80} = 25/80 = 0.3125$$

Segment r is more similar to s than is t.

Because of the redundancy of the integers in the second embodiment, it is possible to come up with sequences that have the same value for example A/G verses A/C., however looking at the chemistry involved in the count are very different. This is an indication of how molecules are communicating differently and therefore not transferring the same information.

For sequences of an entire genome, a normalization technique is used and it is presented in equation (2) below. Thus, in a DNA sequence each position of a nucleotide represents a unique address in the string. In short strands, the denominator is used to measure the intensity of the difference. For longer strands, the normalization technique discussed below in connection with equation (2) is used in which purges the exponential growth of the denominator out. This allows VaSSA to plot each position with respect to its unique address. The omega measure with respect to these unique positions generates unique structural behavior with respect to each nucleotide as well as how it is profiled with respect to the strand it is in.

Computer Program Product

In an exemplary embodiment, the method of the present invention may be embodied on a machine-readable medium, that when read by the machine causes the machine, for example, a computer, to perform the methods described above. In addition, this embodiment of the invention may provide a graphical user interface (GUI) that allows a user to compare sequences of genetic material, and further analyze the sequences and the comparison results.

Figure 3:
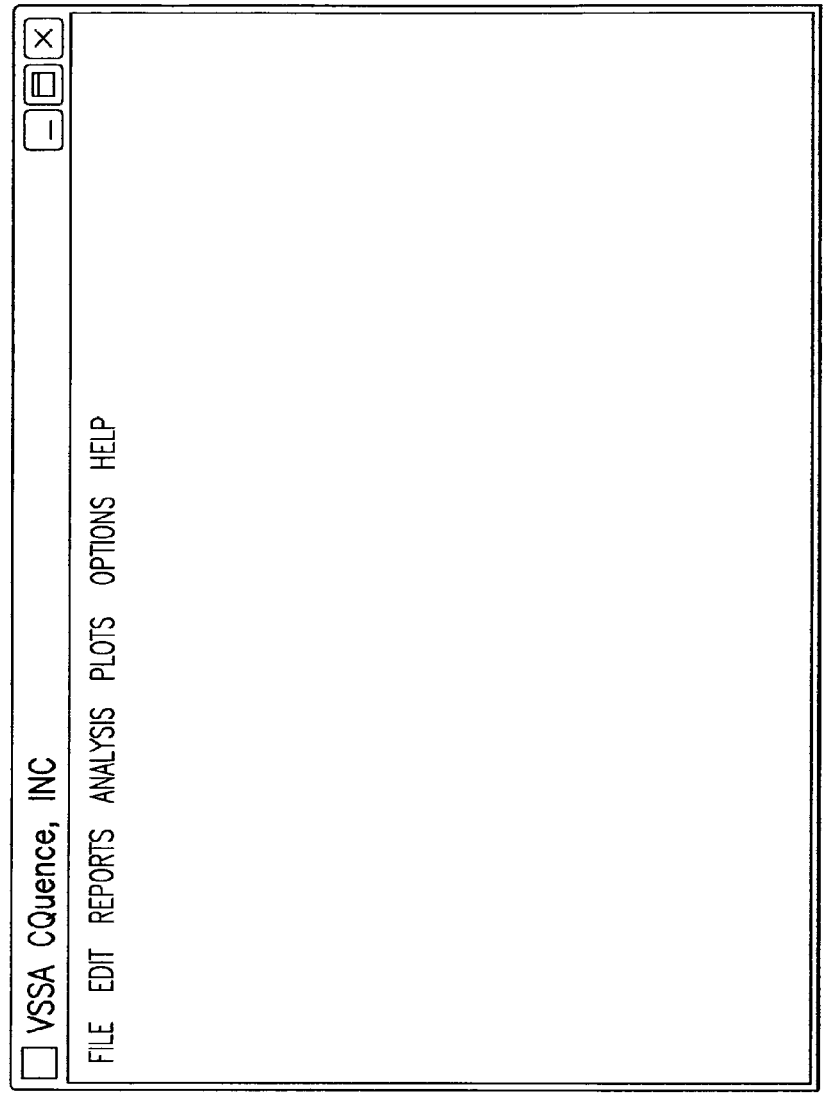
FIG. 3 depicts an exemplary embodiment of a GUI main window in a Variation Sequence Software Application (hereinafter "VaSSA").

For example, as seen in FIG. 3, the GUI may provide modules for file management, reporting, analysis, plotting, setting user options, and user help.

As shown in FIG. 4, the file management module 300 may further include a module to load sequences, which may load one or more sequence files. A file may contain a single sequence or multiple sequences. These sequences can be read off a disk, CD, etc. These sequences does not have to be stored, they could be analyzed "on the fly" as they are received. The sequence files may be FASTA formatted, or any other format. When loaded, each sequence may be assigned a unique reference number, and may be checked to ensure that all characters are valid.

The file management module 300 may also include a module to flush active sequences, which may remove, or "flush", an active sequence file from memory. When flushed, the reference numbers for the sequence are preserved. The file management module 300 may also include a module to flush a loaded sequence from memory. An active sequence is a sequence in which analysis is being carried out on while a loaded sequence is a sequence also in memory but at the present time there is no analysis being done on it.

The module to load sequences may include a module to display a loaded sequence, which may generate and display a summary report notebook page when a sequence is loaded. As shown in FIG. 5, the summary report notebook page may display a sequence file name and a number of sequences.

The report module 500 may generate and display a sequence summary of all loaded sequences including the unique reference number, the sequence header, and the sequence length (FIG. 6); a listing of the contents of each loaded sequence including the unique reference number and the sequence contents in FASTA format (FIG. 7); and/or statistical information about each loaded sequence including the unique reference number, the sequence header, and a count of each standard sequence character (FIG. 8). If a sequence character is not recognized, the reporting module generates a error signal which is listed in an "Error" column in the statistical information about each loaded sequence (FIG. 8).

Figure 9:
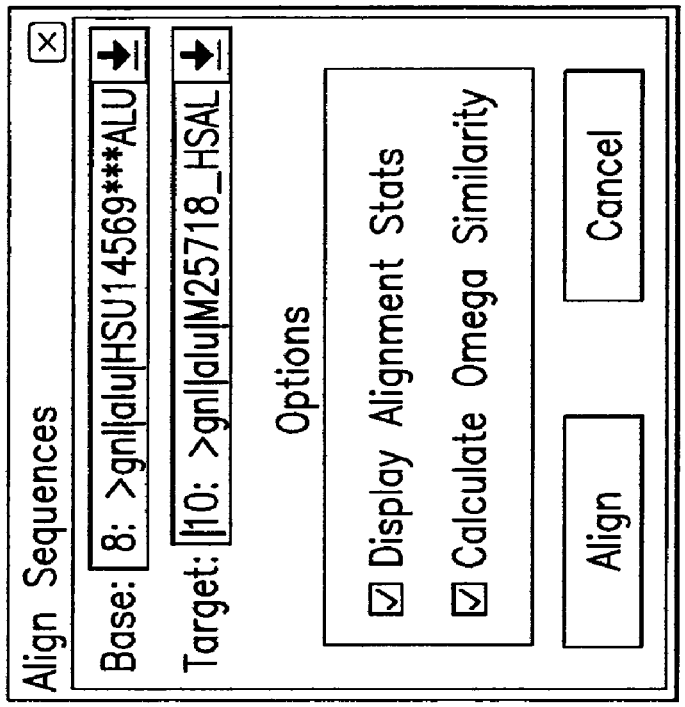
FIG. 9 depicts an exemplary embodiment of a ALIGN SEQUENCE menu window in VaSSA.
Figure 10:
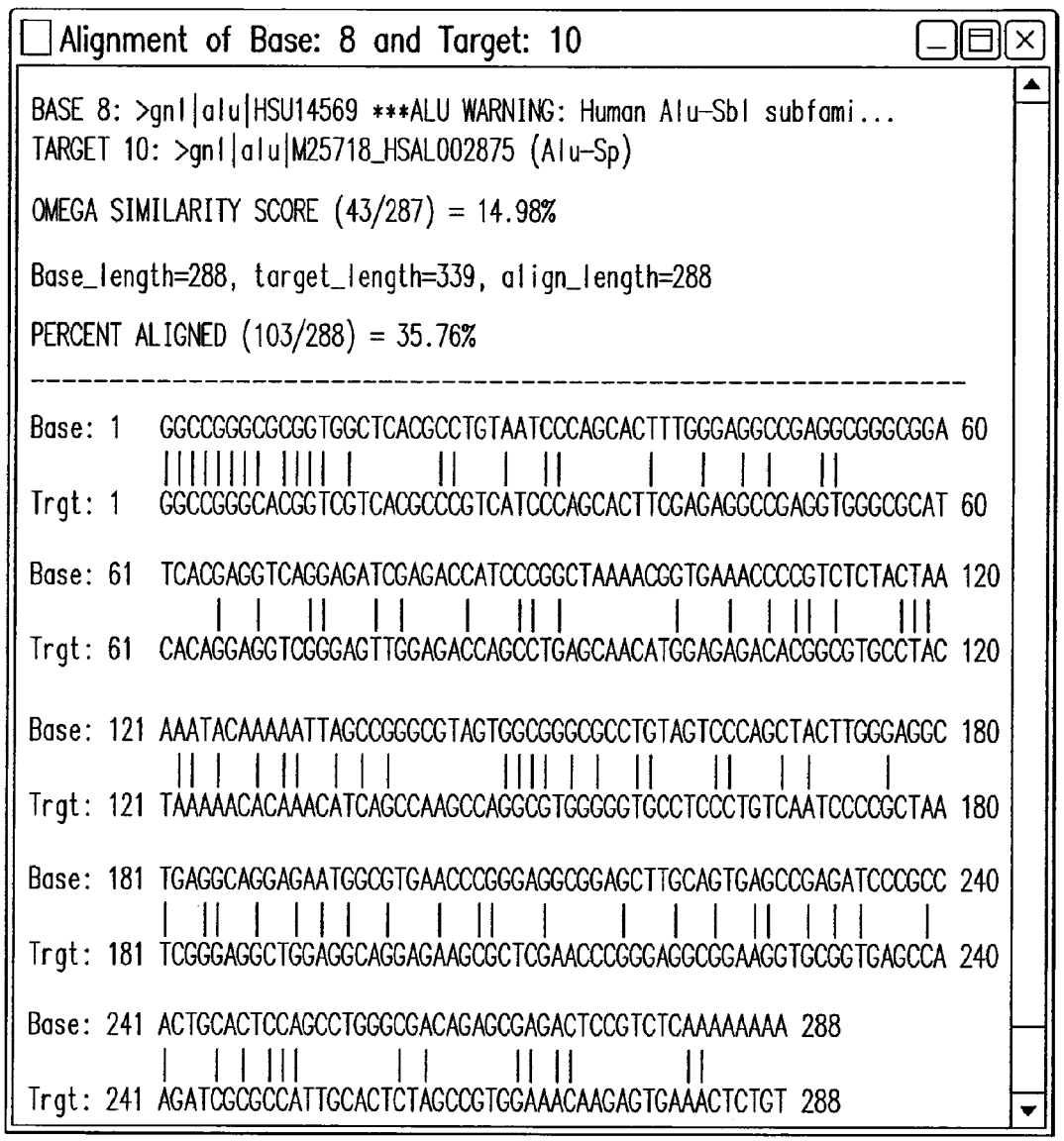
FIG. 10 depicts an exemplary embodiment of an ALIGNED SEQUENCE REPORT window in VaSSA (SEQ ID NOS 5-6 disclosed respectively in order of appearance).

The analysis module 200 may include a number of sub-modules. For example, an align sequences sub-module may align a target sequence to a base sequence and display an alignment report (FIG. 9). The align sequences module may also reverse the base sequence, reverse a mode, align the base and the target to a shortest length, calculate an alignment percentage, or calculate an omega similarity score (FIG. 10). The omega similarity score may be used to determine whether and to what extent the target is similar to the base. If the omega similarity score value is less than $\frac{1}{2}^n$ where n is the maximum length of the two sequences s and t, the two sequences may be said to be similar. If the omega similarity score value is greater than $\frac{1}{2}^n$, then the sequences are said to be dissimilar.

The tasks of the menu options in the VaSSA analysis menu include but not limited to:

1. Reverse Base

Under the analysis menu of VaSSA, is a reverse base option. One function of the Reverse base is to enable the user to change the sequence around. For example if the sequence is 5' to 3' direction then reverse base function reads from the 3' to 5' direction (however not the complement strand direction).

2. Reverse Mod

The function of the Reverse Mod option is to enable one to reverse the mod calculations. "Reversing the mod calculations" means changing $s_{i/ti}$ to $t_i/s_i$. This is significant since by definition $\omega_0$ is not a symmetrical operation.

3. Align Base and Target Sequences to the Shortest Length

The base and target are two sequence strings of different lengths or the same length. If the strings are of different lengths then the first part of the analysis is to align and stop at the end of the shortest sequence. If they are the same length, the sequence analysis is carried out to the end of each string.

4. Calculate Alpha Numeric Alignment Percentage and Omega Similarity Score

Figure 13:
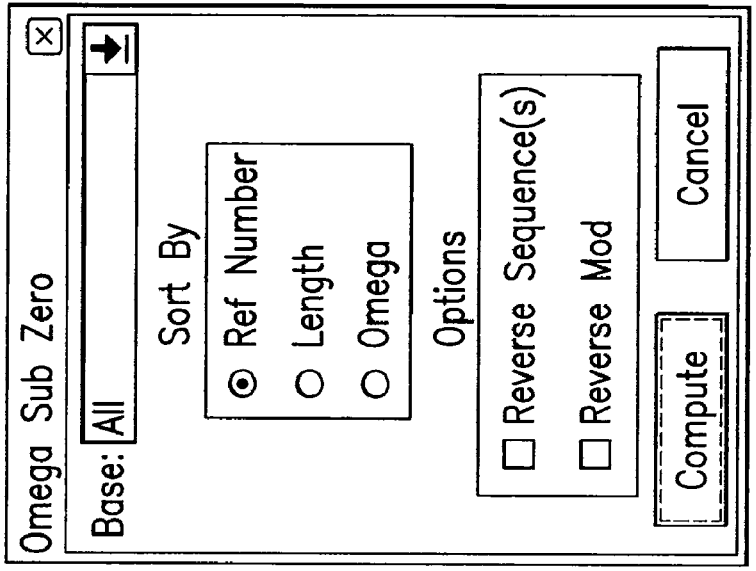
FIG. 13 depicts an exemplary embodiment of an OMEGA SUBZERO window in VaSSA.

The alpha numeric alignment is an alignment which gives a percentage which is the total number of nucleotides aligned over the total number of nucleotides. As shown in FIG. 13, an omega sub-zero ($\omega_0$) module may calculate an $\omega_0$ score for a sequence and display the $\omega_0$ score. One base, or all loaded sequences may be chosen. The report can be sorted by reference number, length, or Omega score (FIG. 14). The base sequence and the mod may each be reversed.

The $\omega_0$ value can also be calculated by the single strand module for the base sequence and the target sequence. Consider the following single strand equation, which is a simplified version of equation 6 (the multiple strand form of the equation will be discussed below):

$$C_l(z_1) = \sum_{\lambda_1 = l} c_{\lambda_1} z_1^{\lambda_1}, l = 0, 1, 2, \ldots \quad (2)$$

where $z_1$ represents a single strand. That is, $z_1 = s_0 s_1 \bigcirc\bigcirc\bigcirc s_k \bigcirc\bigcirc\bigcirc$ where each $s_k$ is an A,G,C or T.

$z_1^{\lambda_i}$ corresponds to the nucleotide in the $\lambda_i$ th position and $\lambda_{i+1}$ th position where i is a number in the index set 1=1,2, 3, . . . .

The coefficients $c_{\lambda_i} = s_i/s_{i+1}$ for the $\lambda$ ith position and i+1 th position where i is a number in the index set 1=1,2,3, . . . .

Figure 27:
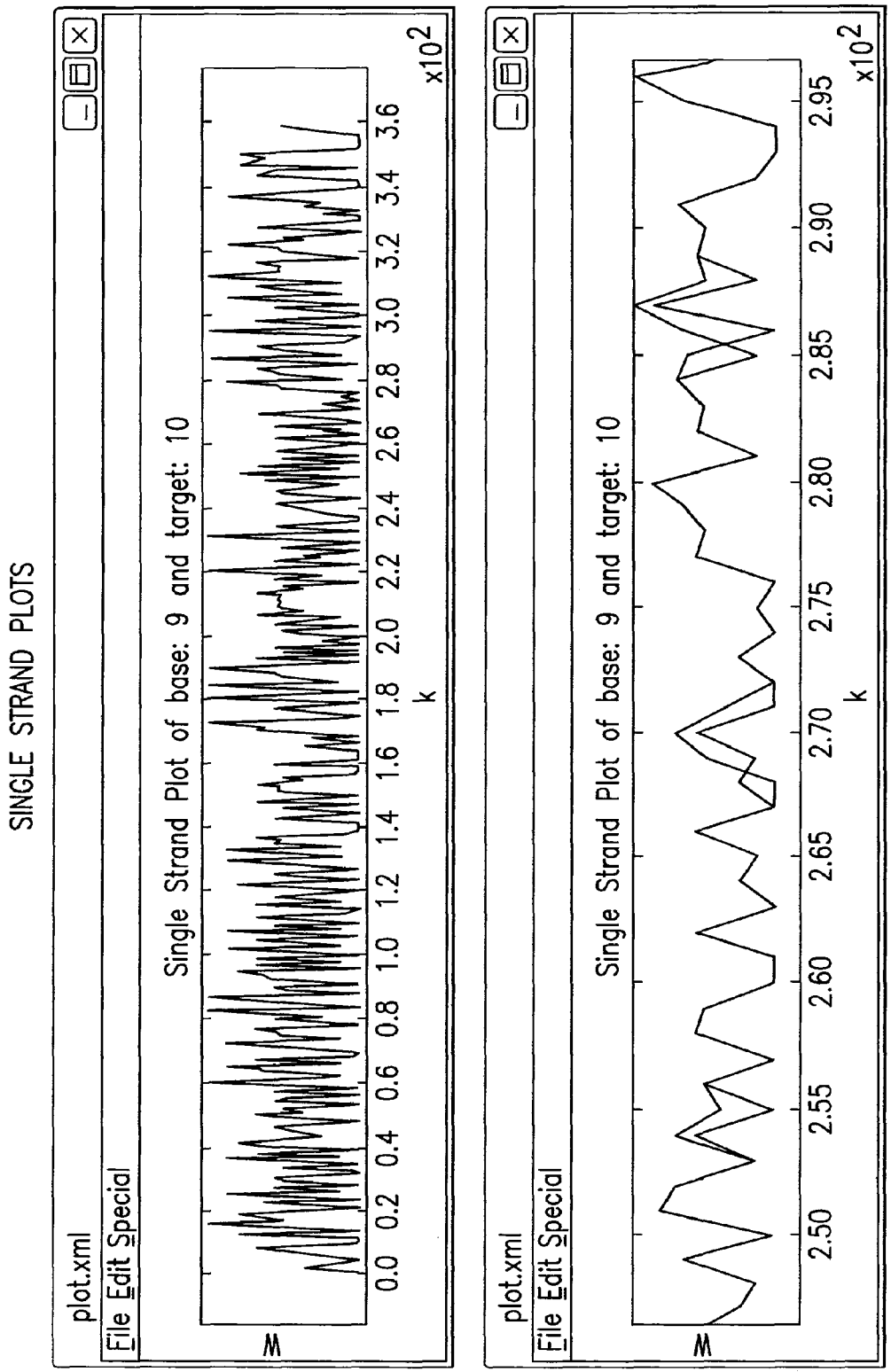
FIG. 27 depicts an exemplary embodiments of SINGLE STRAND PLOT REPORT windows in VaSSA comparing spectral array plots of two 360 base sequences (top) and a region from position 250 to position 295 of those sequences (bottom), with single base resolution.

Thus, for an exemplary four nucleotide strand $z_i$=ACGT, $C_1(z_1)$ is an array of coefficients $[c_0, c_1, c_2]$, where each coefficient is calculated by determining $z_1^{\lambda_i}/z_1^{\lambda_{i+1}}$ for position i in the strand (except for the last position), which is equal to [A/C, C/G, G/T]=[6,7,8] in this case. These coefficients can be used to form a single strand plot for strand $z_1$ in which the position in the strand (in other words, the value of 1) is represented on the x axis and the value of the corresponding coefficient is represented on the y axis (an example of single strand plots for two strands is shown in FIG. 27).

Figure 11:
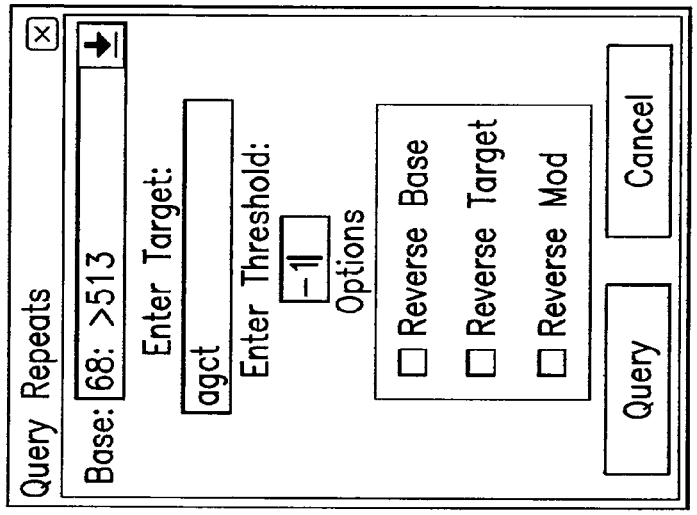
FIG. 11 depicts an exemplary embodiment of a QUERY REPEAT window in VaSSA.

A query repeats module may locate multiple occurrences of a user-specified target sequence in the base sequence and display the multiple occurrences. Multiple occurrences of a target sequence are referred to herein as repeats. VaSSA has two types of repeats: Repeats and Omega repeats. The repeats are just using the shift function on symbols and the Omega repeats use the shift function on the measurement of omega similarity. As shown in FIG. 11, The user may select a base sequence to search, and a target sequence to search for. The user may specify a threshold to relax or tighten the search. The base or target sequences may also be reversed. The query repeat module may then generate sub-targets when the user specifies a threshold and identify positions in the base where the target or sub-target appear. In one embodiment, if the target is AGCT, the query repeat module may generate sub-targets of AGC and GCT. As shown in FIG. 12, the repeat target and subtargets are identified at the top of the GUI window page along with the number of times the repeat target and subtargets are detected. Occurrences of the target sequence are identified with hat symbols 1201 and occurrences of sub-target sequences are identified with asterisk symbols 1202.

Figure 15:
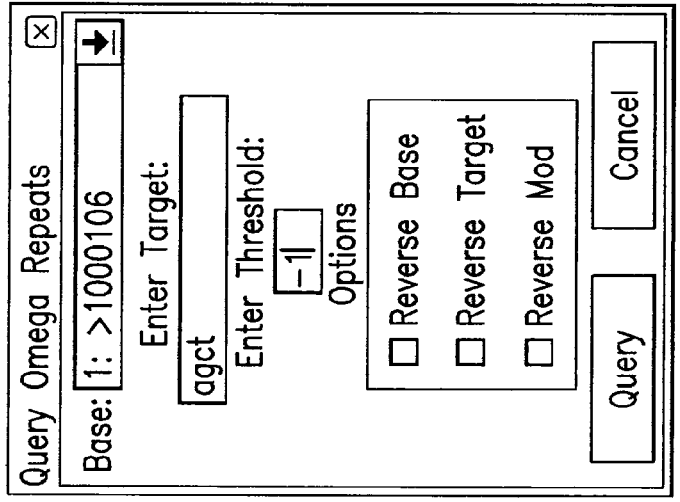
FIG. 15 depicts an exemplary embodiment of a QUERY OMEGA REPEAT MENU window in VaSSA.

As shown in FIGS. 15 and 16, a query omega repeats module obtains everything aforementioned with respect to the query repeat module. However, in addition, it picks up how repeated nucleotides in a segment of a string may be communicating differently (at least with respect to the omega measure) in another segment of the string. Thus query omega repeats can pick up when repeats are duplicates and when they are not.

Figure 17:
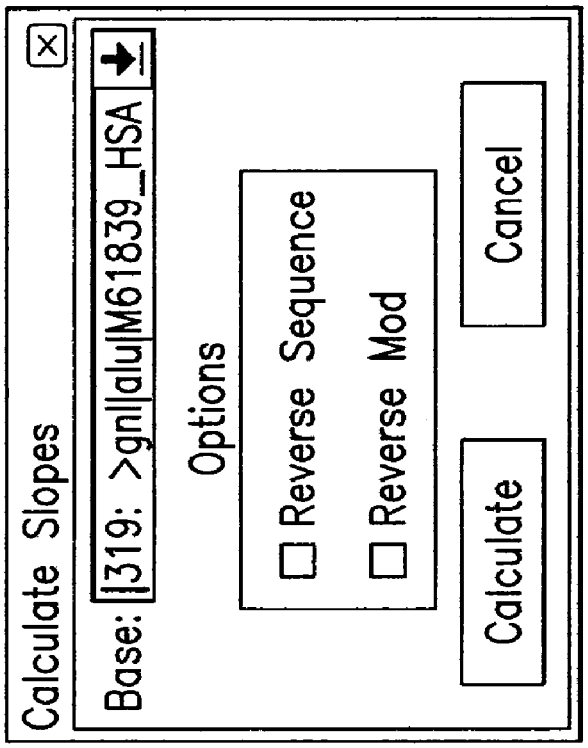
FIG. 17 depicts an exemplary embodiment of a CALCULATE SLOPE window in VaSSA.
Figure 18:
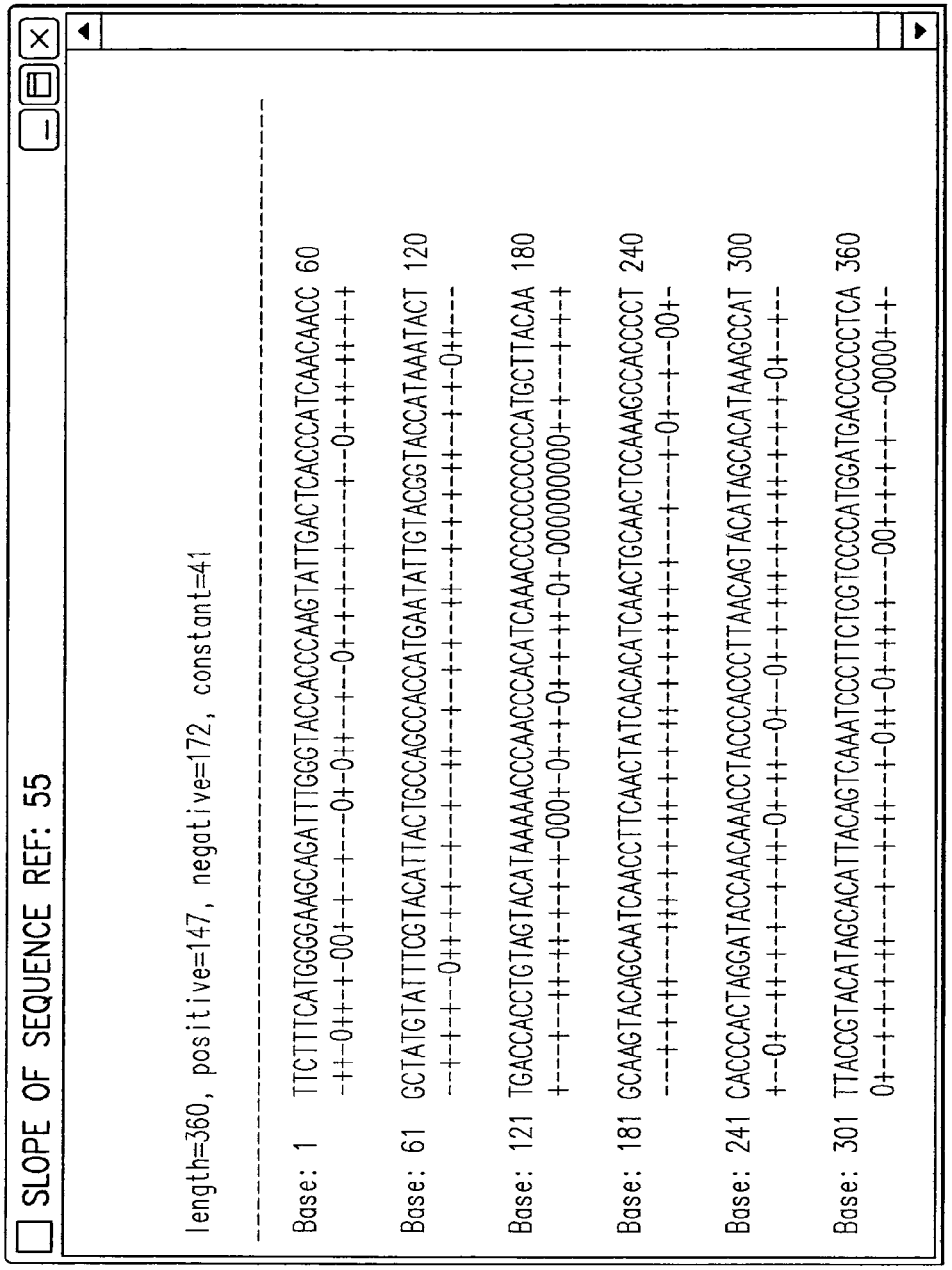
FIG. 18 depicts an exemplary embodiment of a CALCULATE SLOPE REPORT in VaSSA (SEQ ID NO 8).
Figure 30:
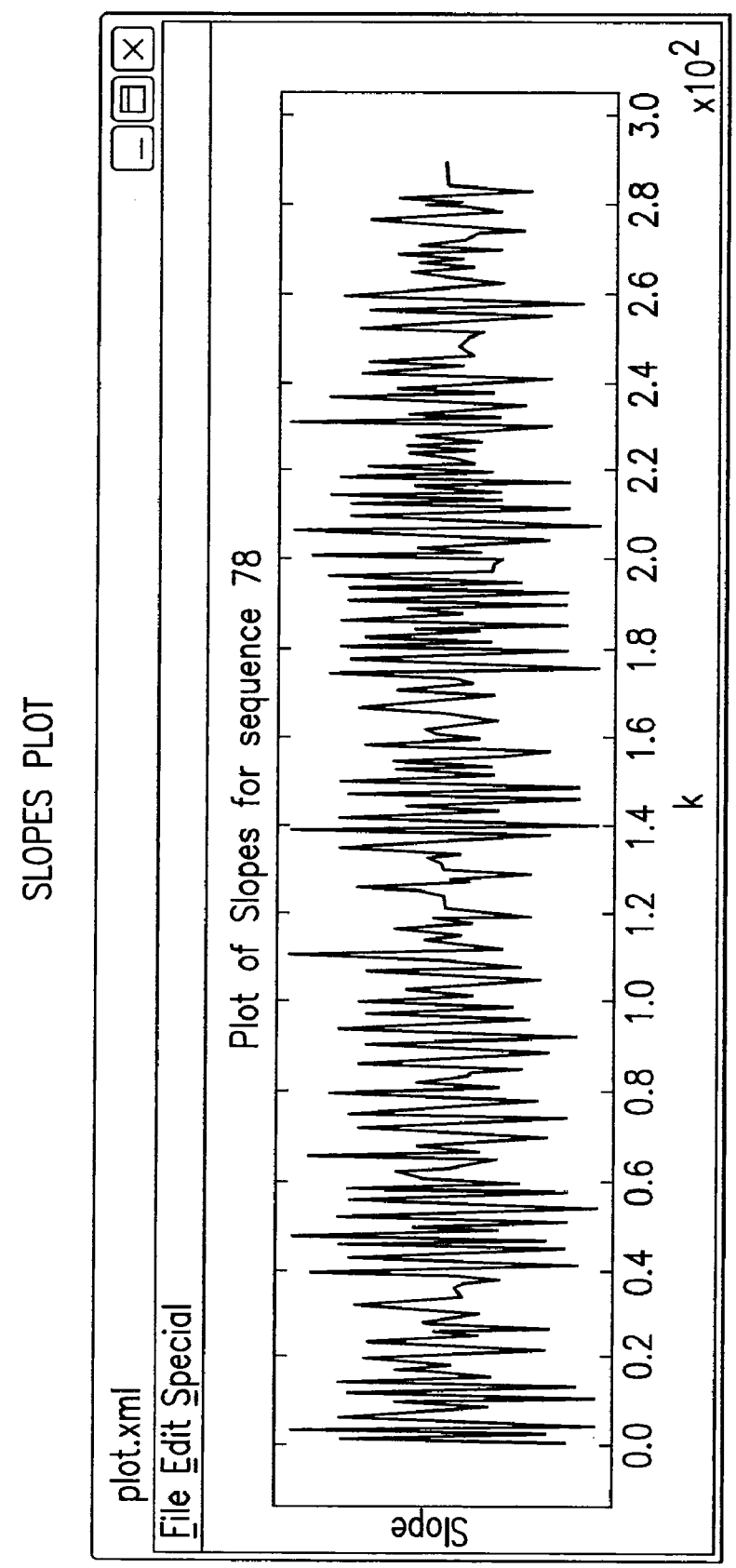
FIG. 30 depicts a slopes plot for a single sequence.
Figure 31:
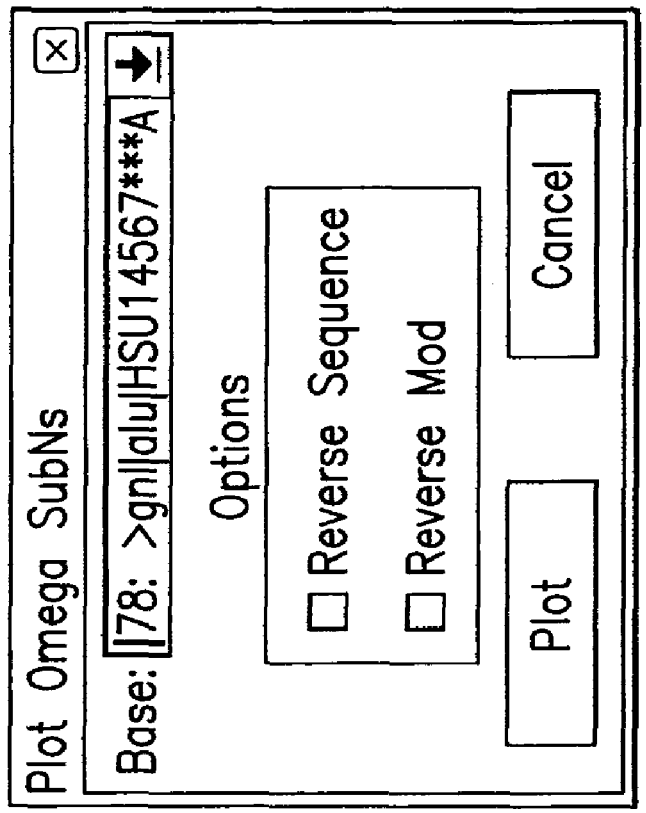
FIG. 31 depicts an exemplary embodiment of an OMEGA SUBN window in VaSSA.
Figure 32:
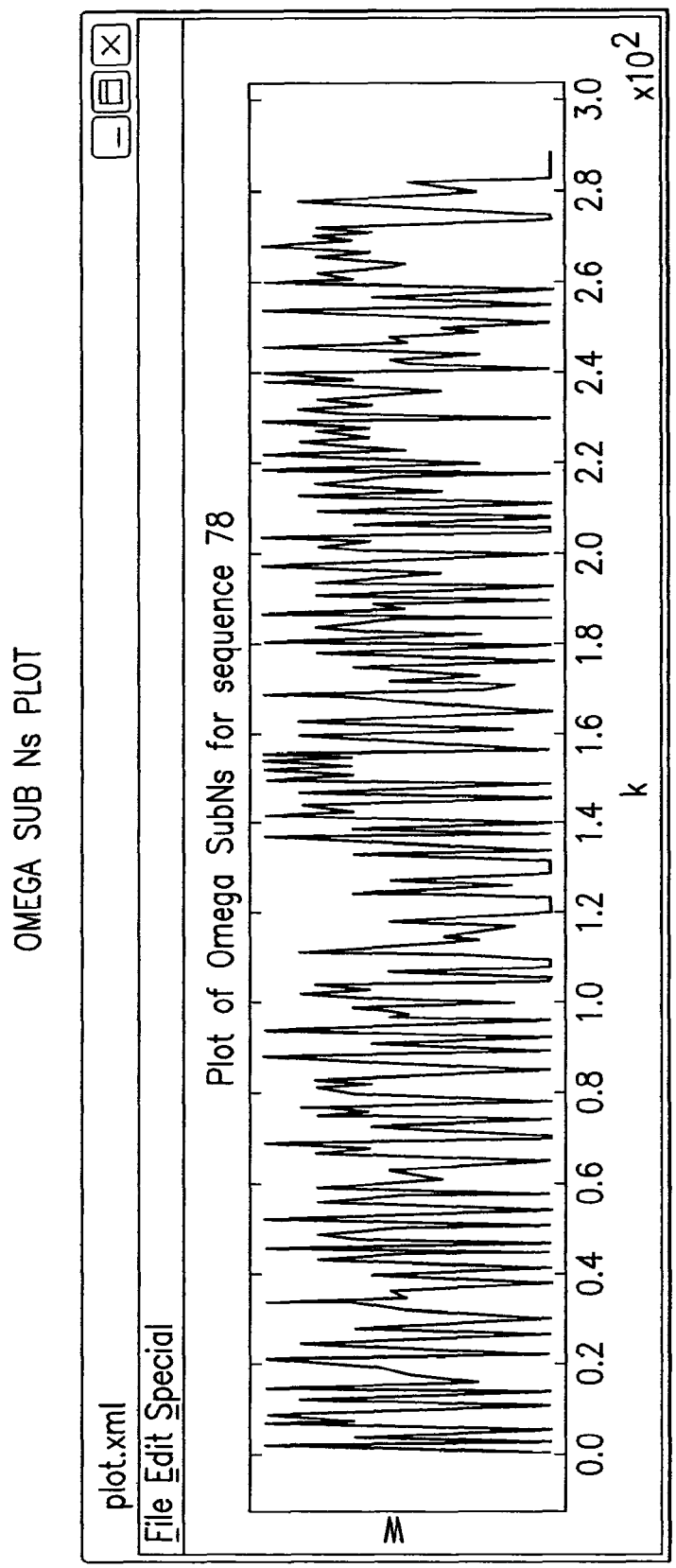
FIG. 32 depicts an exemplary embodiment of an OMEGA SUBN PLOT window in VaSSA.

As shown in FIGS. 17 and 18, a calculate slopes module may calculate a slope for each nucleotide position in a base sequence and display a slopes report. In an exemplary embodiment, the slopes may be calculated using the following:

$$\Omega_k = s_k/s_{k-1} - s_{k-1}/s_k \quad (3)$$

where k represents the unique position of a nucleotide in a DNA sequence. $\omega_k = s_k/s_{k+1}$, $\omega_k$ is the $k^{th}$ term in the $\omega_0$ series. The equation may be used to generate information on curvature in the 2-D profiles. When $\Omega_k$ is positive, the information being transferred is increasing and the bonds that connect the double strand are longer (and thus have a tendency to be weaker than shorter ones). When $\Omega_k$ is negative, the information being transferred is decreasing and the bonds are shorter connecting the double helix (and have a tendency to be stronger). Thus, in a plot of the positives and negatives is a profile of information flows from one position to the next in a sequence. The slope graph is a plot of the change information flow. It shows where information change is the same in the sequence (with zeros in sign chart) and different. It also shows where information is exactly the same but in the opposite direction. To generate the graph, (an example of which is shown in FIG. 30) the position of the nucleotide is plotted against the value of the slope. Thus, equation 3 is what generates the sign charts and the slope plots in VaSSA. In both cases, the nucleotide unique position in a strand corresponds to the x-axis and the value of $\Omega_k$ corresponds to the y-axis.

In one embodiment, in a sequence AGC, the change from A to G would be calculated as follows: A is at position k-1, G is at k, and C is at k+1. Omega(k), based on the values in Table 2, is then G/C−A/G=10−6=4. The change from A to G is therefore positive, and may be represented by a "+" in the slopes report.

Figure 19:
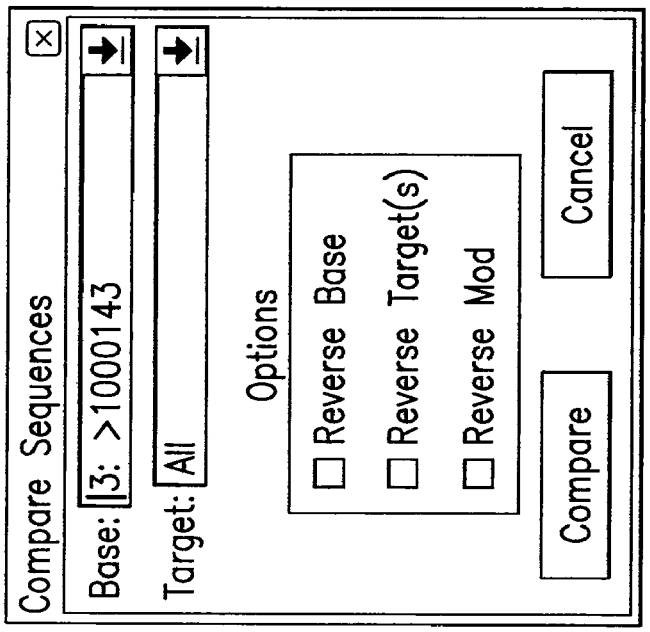
FIG. 19 depicts an exemplary embodiment of a COMPARE SEQUENCE window in VaSSA.
Figure 21:
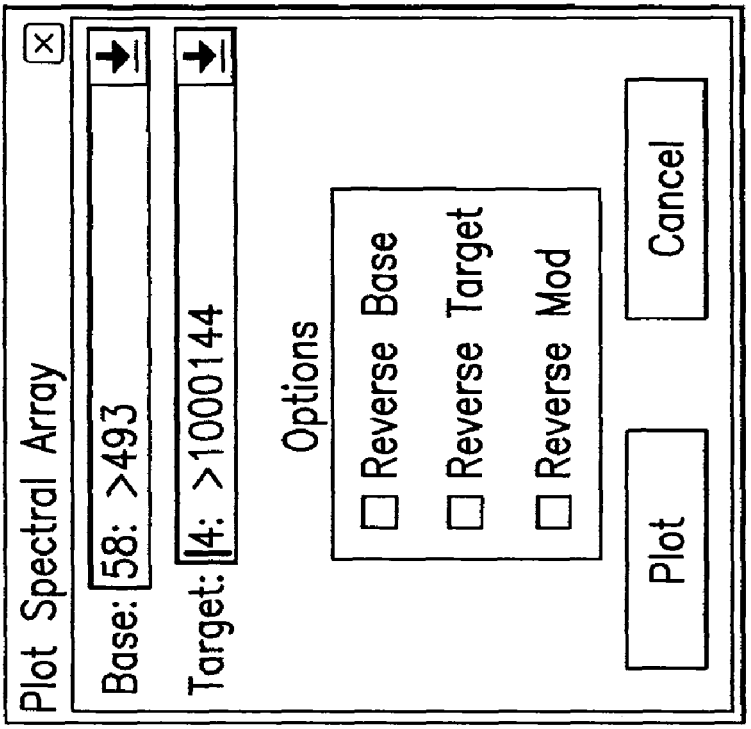
FIG. 21 depicts an exemplary embodiment of a SPECTRAL ARRAY window in VaSSA.
Figure 22:
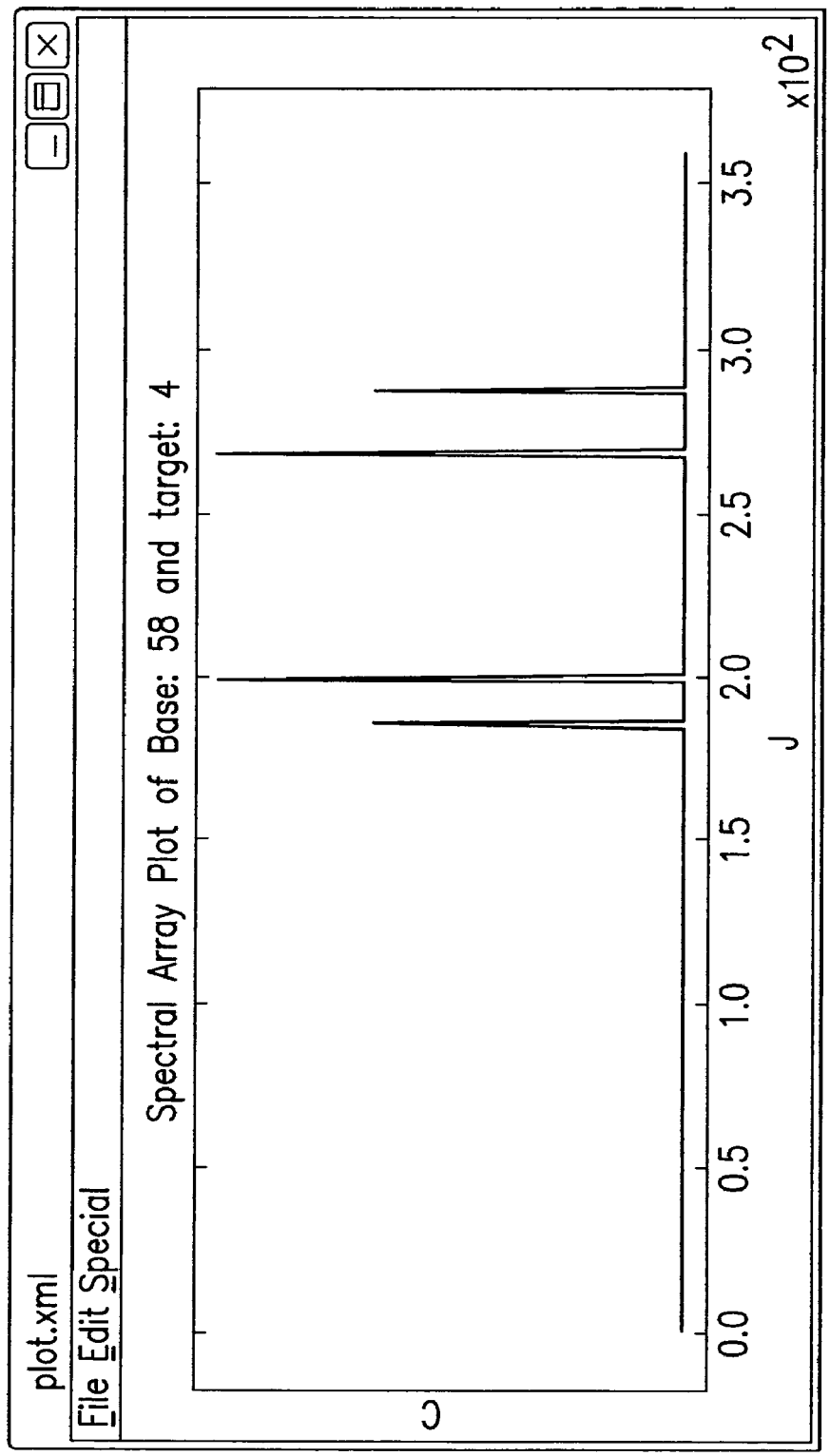
FIG. 22 depicts an exemplary embodiment of a SPECTRAL ARRAY PLOT window in VaSSA.

As shown in FIGS. 19 and 20, a compare sequences sub-module may compare the target sequence to the base sequence and display a similarity report. The compare sequences sub-module may also reverse the base sequence, reverse the target sequence, reverse a mode, calculate an $\omega_n$ value for each of the base and target sequences, convert the base and the target sequences to binary, calculate a distance between the base sequence and the target sequence, and determine if the distance exceeds a bound.

As shown in FIGS. 21-25, the plots module may include a number of plotting sub-modules. For example, a spectral array sub-module may plot aligning coefficients for a base sequence and a target sequence. The spectral array sub-module may also calculate an $\omega_n$ value for radial compare, and extract aligning coefficients. In a radial comparison, the spectral array sub-module may use the formulas:

$$f(\vec{z}) = \sum_{l=0}^{\infty} C_l(\vec{z}) \quad (4)$$

where $$c_l(\vec{z}) = \sum_{\lambda_1+\lambda_2+\ldots+\lambda_n=1} c_{\lambda_1 \lambda_2 \ldots \lambda_n} z_1^{\lambda_1} z_2^{\lambda_{21}} \ldots z_n^{\lambda_{n1}}, l = 0, 1, 2, \ldots \quad (5)$$

This formula is for multiple sequences. It allows the generation of a unique spectral analysis is a notation that is used for multiple sums with respect to 1. These are the coefficients generated in each sequence with respect to $\omega_0$ to their positions. The nucleotide in each sequence position is denoted by $Z_1^{\lambda_1} Z_2^{\lambda_{21}} \bullet\bullet\bullet Z_n^{\lambda_{n1}}$.

Figure 24:
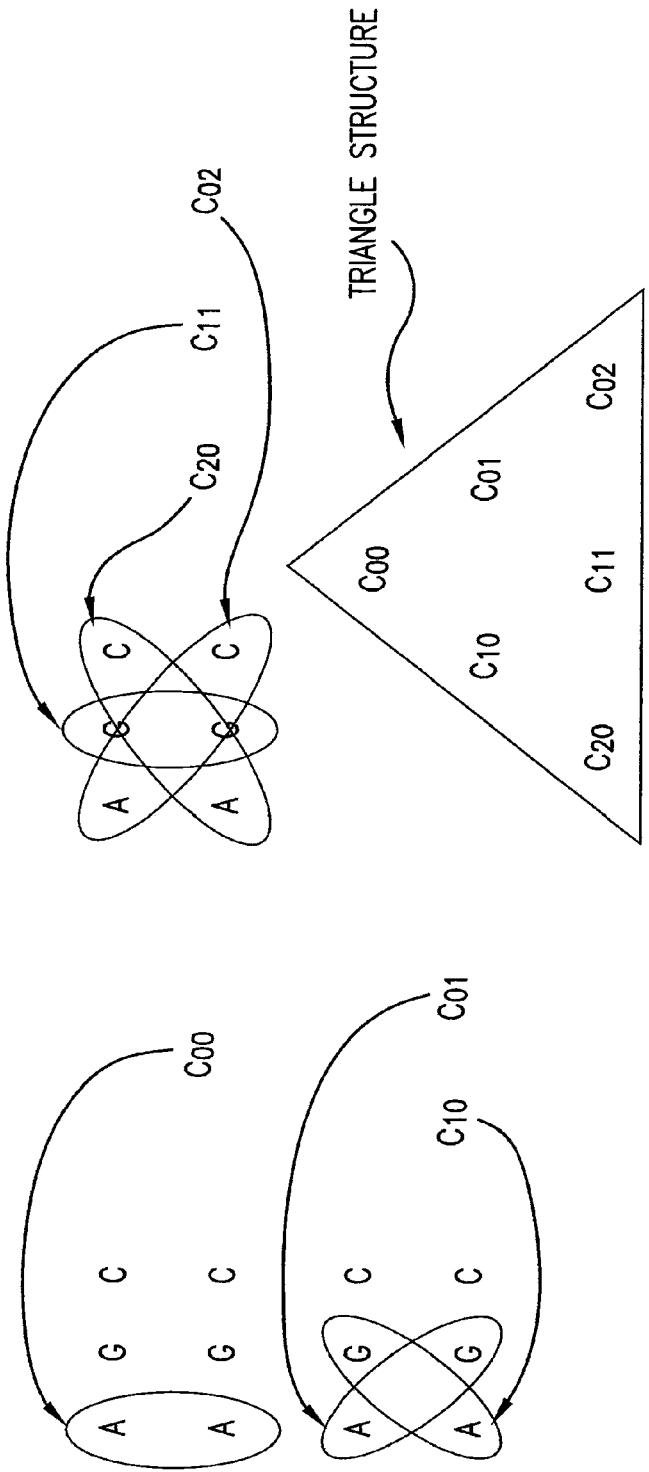
FIG. 24 depicts a schematic drawing of a spectral array formula example.
Figure 25:
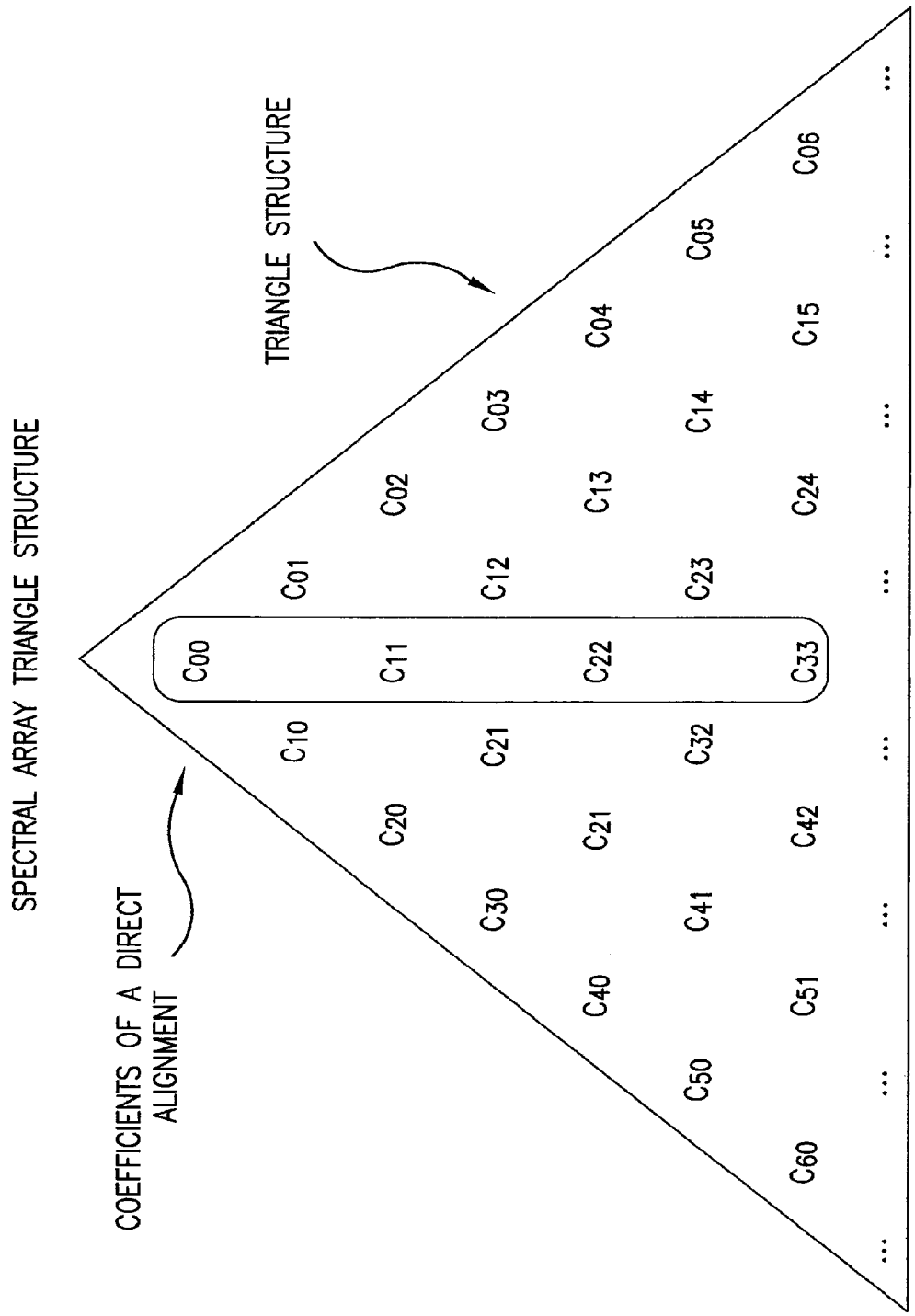
FIG. 25 depicts a picture of a SPECTRAL ARRAY TRIANGLE STRUCTURE.

The formation of equations 4 and 5 allows the generation of the plots in VaSSA. The Coefficient Structure of the formula can be captured in a triangle structure which is presented in FIG. 25. The spectral structure is triangle allows to observe optimization without inserting or deleting spaces in strands of DNA. FIG. 24 demonstrates with two strands of how the coefficients are being generated when the formula was used. The single strand plot has the same structure but different values. Because of the non-binary measure, it can be precisely observed that where the plots are equivalent and where they are different. It can also be observed that where there is periodicity. Since the function is analytical, it can be formulated shifts without effecting the uniqueness of nucleotide location. One embodiment is shown in FIG. 27. The spectral array plot in VaSSA uses the coefficients right down the center of the triangle structure on FIG. 25. An example of this plot is FIG. 22. This has information where they have direct alignment because is the graph is zero their. There are also spikes with a certain heights. Similar information can be observe as single strand plot. But the magnitude of the difference can be visualized here with respect to the height of the spikes. Also with pointers in the triangles we can a complete phase portrait which is a different way to do optimization.

Figure 26:
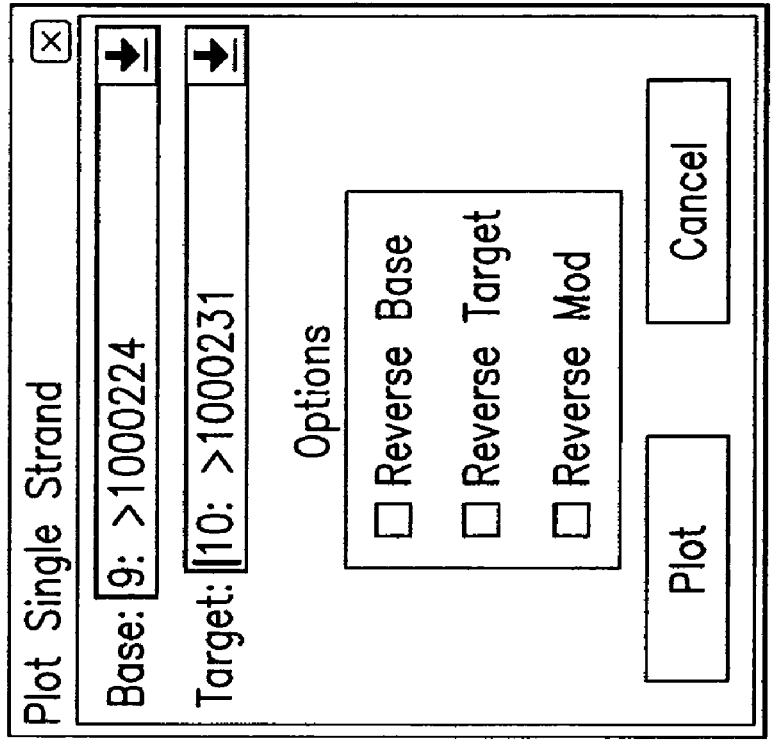
FIG. 26 depicts an exemplary embodiment of a SINGLE STRAND window in VaSSA.

As shown in FIGS. 26-28, a single strand sub-module may plot a single strand for the base sequence and the target sequence. The single strand sub-module may also calculate an $\omega_n$ value for the base sequence and the target sequence. The single strand sub-module may plot using equation (4), where $$C_l(\vec{z}) = \sum_{\lambda_{11}=l} c\lambda_1 z_1^{\lambda_1}, l = 0, 1, 2, \ldots \quad (6)$$

is a simplified version of equation (5). However this equation allows one to profile a single strand.

Figure 29:
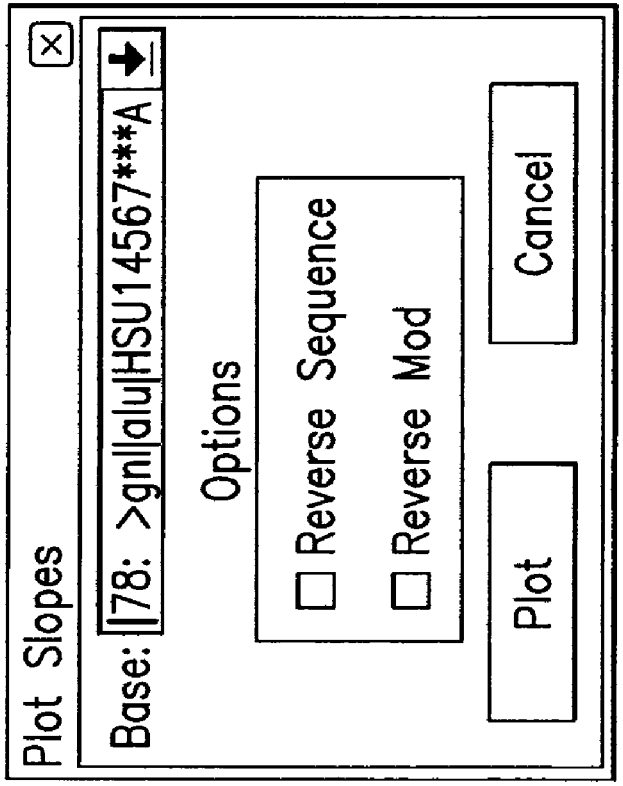
FIG. 29 depicts an exemplary embodiment of a Plot Slopes window in VaSSA.

As shown in FIGS. 29-30, a slopes module may calculate a slope for each nucleotide position in the base sequence and display a plot of the slopes. A $\omega_n$ module may calculate $\omega_n$ for the base sequence and display a plot of $\omega_n$. The $\omega_n$ module may use equation (6).

The generate plot of slope will generate the plot on FIG. 30. The slope plot is a graph of the montonicity of information flow. This plot allows a user to determine local and global max, and min position on single strand plots. It also allows a user to determine concavities in local areas as well as global areas of the single strand plot.

While various embodiments of the present invention have been described above, it should be understood that they have been presented by way of example only, and not limitation. Thus, the breadth and scope of the present invention should not be limited by any of the above-described exemplary embodiments, but should instead be defined only in accordance with the following claims and their equivalents.

What is claimed is:

1. A system for sequence analysis, comprising:
   a computer system comprising
   an analysis module, adapted to calculate a non-binary similarity score between a first nucleotide sequence and a second nucleotide sequence; and
   an output in communication with the analysis module for outputting the similarity score,
   wherein said non-binary similarity score is calculated by pairing nucleotides of said first nucleotide sequence with nucleotides of said second nucleotide sequence, obtaining a similarity score for each base pair between said first nucleotide sequence and said second nucleotide sequence, and combining similarity scores of all base pairs between said first nucleotide sequence and said second nucleotide sequence, wherein the similarity score for a base pair $s_i/t_i$ is a non-binary score that is calculated by counting the number of atoms present in the nucleotide $s_i$ that are not present in the nucleotide $t_i$.

2. The system of claim 1, wherein the similarity score for a base pair is a first value if the nucleotides in said base pair are the same, a second value if the nucleotides in said base pair are different but are both purines or pyrimidines, or a third value if one nucleotide in said base pair is a purine and another nucleotide in said base pair is a pyrimidine, and wherein the first, second and third values are different from each other.

3. The system of claim 2, wherein the second value or the third value is further modified by a degree of differences between the chemical structure of the nucleotides in the base pair.

4. The system of claim 1, further comprising a graphical user interface (GUI) that comprises a report module adapted to provide reports on loaded sequences; a file management module adapted to manage sequence files; and a plot module adapted to provide sequence analysis plots.

5. The system of claim 4, wherein the GUI further comprising a user options module adapted to provide user preferences.

6. The system of claim 4, wherein said file management module comprises:
   a load sequence module, adapted to load at least one sequence file;
   a flush active sequence module, adapted to flush a sequence file from a memory; and
   a flush loaded sequence module, adapted to flush a loaded sequence file from said memory.

7. The system of claim 6, wherein said load sequence module comprises:

a loaded sequence display module, adapted to generate and display a summary report notebook page when a sequence is loaded, wherein said summary report notebook page is adapted to display a sequence file name and a number of sequences.

8. The system of claim 4, wherein said report module is adapted to generate and display at least one of:

a sequence summary;
a listing of the contents of each loaded sequence, or statistical information about each loaded sequence.

9. The system of claim 1, wherein said analysis module comprises a single-strand DNA analysis module and a multi-strand DNA analysis module.

* * * * *

SEQUENCE LISTING

<160> NUMBER OF SEQ ID NOS: 8

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agcaatatag ga                                                          12

<210> SEQ ID NO 2
<211> LENGTH: 288
<212> TYPE: DNA

<213> ORGANISM: Homo sapiens

<400> SEQUENCE: 2

```
ggccgggcgc ggtggctcac gcctgtaatc ccagcacttt gggaggccga ggcgggcgga    60
tcacgaggtc aggagatcga gaccatcctg gctaacacgg tgaaacccccg tctctactaa   120
aaatacaaaa attagccggg cgtggtggcg ggcgcctgta gtcccagcta ctcgggaggc   180
tgaggcagga gaatggcgtg aacccgggag gcggagcttg cagtgagccg agatcgcgcc   240
actgcactcc agcctgggcg acagagcgag actccgtctc aaaaaaaa                288
```

<210> SEQ ID NO 3
<211> LENGTH: 290
<212> TYPE: DNA
<213> ORGANISM: Homo sapiens

<400> SEQUENCE: 3

```
ggccgggcgc ggtggctcac gcctgtaatc ccagcacttt gggaggccga ggcgggcgga    60
tcacctgagg tcaggagttc gagaccagcc tggccaacat ggtgaaaccc cgtctctact   120
aaaaatacaa aaattagccg ggcgtggtgg cgcgcgcctg taatcccagc tactcgggag   180
gctgaggcag gagaatcgct tgaacccggg aggcggaggt tgcagtgagc cgagatcgcg   240
ccactgcact ccagcctggg cgacagagcg agactccgtc tcaaaaaaaa               290
```

<210> SEQ ID NO 4
<211> LENGTH: 291
<212> TYPE: DNA
<213> ORGANISM: Homo sapiens

<400> SEQUENCE: 4

```
ggccgggcgc ggtggctcac gcctgtaatc ccagcacttt gggaggccga ggcgggcgga    60
tcacctgagg tcgggagttc gagaccagcc tgaccaacat ggagaaaccc cgtctctact   120
aaaaatacaa aaattagccg ggcgtggtgg cgcatgcctg taatcccagc tactcgggag   180
gctgaggcag gagaatcgct tgaacccggg aggcggaggt tgcggtgagc cgagatcgcg   240
ccattgcact ccagcctggg caacaagagc gaaactccgt ctcaaaaaaa a             291
```

<210> SEQ ID NO 5
<211> LENGTH: 288
<212> TYPE: DNA
<213> ORGANISM: Homo sapiens

<400> SEQUENCE: 5

```
ggccgggcgc ggtggctcac gcctgtaatc ccagcacttt gggaggccga ggcgggcgga    60
tcacgaggtc aggagatcga gaccatcccg gctaaaacgg tgaaacccccg tctctactaa   120
aaatacaaaa attagccggg cgtagtggcg ggcgcctgta gtcccagcta cttgggaggc   180
tgaggcagga gaatggcgtg aacccgggag gcggagcttg cagtgagccg agatcccgcc   240
actgcactcc agcctgggcg acagagcgag actccgtctc aaaaaaaa                288
```

<210> SEQ ID NO 6
<211> LENGTH: 288
<212> TYPE: DNA
<213> ORGANISM: Homo sapiens

<400> SEQUENCE: 6

```
ggccgggcac ggtcgtcacg cccgtcatcc cagcacttcg agaggccgag gtgggcgcat    60
cacaggaggt cgggagttgg agaccagcct gagcaacatg gagagacacg gcgtgcctac   120
```

```
taaaaacaca aacatcagcc aagccaggcg tgggggtgcc tccctgtcaa tccccgctaa      180
tcgggaggct ggaggcagga gaagcgctcg aacccgggag gcggaaggtg cggtgagcca      240
agatcgcgcc attgcactct agccgtggaa acaagagtga aactctgt                  288

<210> SEQ ID NO 7
<211> LENGTH: 360
<212> TYPE: DNA
<213> ORGANISM: Homo sapiens

<400> SEQUENCE: 7
ttctttcatg gggaagcaga tttgggtacc acccaagtat tgactcaccc atcaacaacc      60
gctatgtatt tcgtacatta ctgccagcca ccatgaatat tgtacagtac cataaatact     120
tgaccacctg tagtacataa aaacccaatc cacatcaaaa ccctcccctc atgcttacaa     180
gcaagtacag caatcaacct tcaactatca cacatcaact gcaactccaa agccacctct     240
cccccactag gataccaaca aagctaccca tccttaacag tacatagcac ataaagccat     300
ttaccgtaca tagcacatta cagtcaaatc ccttcctgtc cccatggatg acccccctca     360

<210> SEQ ID NO 8
<211> LENGTH: 360
<212> TYPE: DNA
<213> ORGANISM: Homo sapiens

<400> SEQUENCE: 8
ttctttcatg gggaagcaga tttgggtacc acccaagtat tgactcaccc atcaacaacc      60
gctatgtatt tcgtacatta ctgccagcca ccatgaatat tgtacggtac cataaatact     120
tgaccacctg tagtacataa aaacccaacc cacatcaaac ccccccccc atgcttacaa      180 gcaagtacag caatcaacct tcaactatca cacatcaact gcaactccaa agccaccct     240 cacccactag gataccaaca aacctaccca cccttaacag tacatagtac ataaagccat    300
ttaccgtaca tagcacatta cagtcaaatc ccttctcgtc cccatggatg acccccctca    360
```